US011597748B2

(12) United States Patent
Chung et al.

(10) Patent No.: US 11,597,748 B2
(45) Date of Patent: Mar. 7, 2023

(54) PEPTIDE HAVING CYTOPROTECTIVE EFFECT AGAINST ENVIRONMENTAL POLLUTANT AND USE THEREOF

(71) Applicant: CAREGEN CO., LTD., Anyang-si (KR)

(72) Inventors: Yong Ji Chung, Yongin-si (KR); Eun Mi Kim, Yongin-si (KR); Eung-ji Lee, Anyang-si (KR)

(73) Assignee: CAREGEN CO., LTD., Anyang-si (KR)

( * ) Notice: Subject to any disclaimer, the term of this patent is extended or adjusted under 35 U.S.C. 154(b) by 31 days.

(21) Appl. No.: 17/391,261

(22) Filed: Aug. 2, 2021

(65) Prior Publication Data

US 2021/0371464 A1 Dec. 2, 2021

Related U.S. Application Data

(63) Continuation of application No. 16/497,056, filed as application No. PCT/KR2018/001953 on Feb. 14, 2018, now Pat. No. 11,104,704.

(30) Foreign Application Priority Data

Mar. 30, 2017 (KR) .......................... 10-2017-0040514

(51) Int. Cl.
| C07K 7/06 | (2006.01) |
| A61K 8/64 | (2006.01) |
| A61K 38/00 | (2006.01) |
| A61Q 19/00 | (2006.01) |
| A61Q 7/00 | (2006.01) |
| A23L 33/18 | (2016.01) |

(52) U.S. Cl.
CPC ............... *C07K 7/06* (2013.01); *A23L 33/18* (2016.08); *A61K 8/64* (2013.01); *A61K 38/00* (2013.01); *A61Q 19/00* (2013.01); *A23V 2002/00* (2013.01)

(58) Field of Classification Search
CPC . C07K 7/06; A61K 8/64; A61K 38/00; A61Q 19/00; A61Q 7/00; A23L 33/18
See application file for complete search history.

(56) References Cited

U.S. PATENT DOCUMENTS

| 6,630,331 | B1 | 10/2003 | Abell et al. |
| 8,067,671 | B2 | 11/2011 | Boukharov et al. |
| 8,344,211 | B2 | 1/2013 | Alexandrov et al. |
| 9,884,910 | B2 | 2/2018 | Fromond et al. |
| 11,104,704 | B2 | 8/2021 | Chung et al. |
| 2005/0153882 | A1 | 7/2005 | Gordon et al. |
| 2008/0038838 | A1 | 2/2008 | Nakamura et al. |
| 2020/0377550 | A1 | 12/2020 | Chung et al. |

FOREIGN PATENT DOCUMENTS

| JP | 2003-231697 A | 8/2003 |
| KR | 2003-0003671 A | 1/2003 |
| KR | 2003-0003672 A | 1/2003 |
| KR | 10-2006-0035432 A | 4/2006 |

OTHER PUBLICATIONS

Extended European Search Report dated Sep. 25, 2020 for European Patent Application No. 18774488.3, Ji et al., "Peptide having Cytoprotective Effect Against Environmental Pollutant and Use Thereof," filed Feb. 14, 2019 (9 pages).
International Search Report dated Jun. 11, 2018 for PCT International Application No. PCT/KR2018/001953, Chung et al., "Peptide Having Cytoprotective Effect Against Environmental Pollutant and Use Thereof," filed Feb. 14, 2018 (6 pages).
Inuyama et al., "Simple and high-sensitivity detection of dioxin using dioxin-binding pentapeptide," Biosens Bioelectron. 22(9-10):2093-9 (2007).
Levinbook et al., "Alopecia Areata," The Merck Manual, retrieved Nov. 2, 2020 <https://www.merckmanuals.com/professional/dermatologic-disorders/hair-disorders/alopecia-areata> (3 pages).
Levinbook, W., "Alopecia (Hair Loss; Baldness)," The Merck Manual <https://www.merckmanuals.com/professional/dermatologic-disorders/hair-disorders/alopecia>, retrieved Nov. 2, 2021 (9 pages).
Mark, J., "Prostate Cancer," The Merck Manual, <https://www.merckmanuals.com/professional/genitourinary-disorders/genitourinary-cancer/prostate-cancer>, retrieved Jan. 12, 2021 (10 pages).
Morita et al., "Chapter 17: Synthesis and Analysis of Peptide Ligand for Biosensor Application Using Combinatorial Chemistry, Screening and Characterization of 2,3,7-Trichlorodibenzo-p—dioxin-Binding Peptide," Biological Systems Engineering. American Chemical Society. 830:210-219 (2002).
Nakamura et al., "Dioxin-binding pentapeptide for use in a high-sensitivity on-bead detection assay," Anal Chem. 77(23):7750-7757 (2005).
Office Action dated Feb. 9, 2021 for Indonesian Patent Application No. P00201909573, Chung et al., "Peptide Having Cytoprotective Effect Against Environmental Pollutant and Use Thereof," filed Feb. 14, 2018 (6 pages).
Pandini et al., "Detection of the TCDD binding-fingerprint within the Ah receptor ligand binding domain by structurally driven mutagenesis and functional analysis," Biochemistry 48(25):5972-5983 (2009).

(Continued)

*Primary Examiner* — Julie Ha
(74) *Attorney, Agent, or Firm* — Clark & Elbing LLP; Susan M. Michaud

(57) ABSTRACT

Provided are a peptide with a cytoprotective effect against environmental pollutants and a use thereof. The peptide consisting of an amino acid sequence of SEQ ID NO: 1, 2, or 3 directly binds to 2,3,7,8-tetrachlorodibenzo-p-dioxin (hereinafter, referred to as TCDD), known as being the most toxic among the class of dioxins, to prevent dermal penetration and the activation mechanism of AhR by TCDD and polycyclic aromatic hydrocarbons contained in fine dust. Such a direct cytoprotective effect against environmental pollutants is distinguished from preexisting methods that are configured to indirectly block opportunities to contact these materials or to reduce toxicity through barrier reinforcement.

7 Claims, 19 Drawing Sheets

Specification includes a Sequence Listing.

(56) References Cited

OTHER PUBLICATIONS

Ramirez et al., "Endometrial Cancer (Uterine Cancer)," The Merck Manual, <https://www.merckmanuals.com/professional/gynecology-and-obstetrics/gynecologic-tumors/endometrial-cancer>, retreived Jan. 12, 2021 (3 pages).
Stavis, R., "Birth Injuries," The Merck Manual, <https://www.merckmanuals.com/professional/pediatrics/perinatal-problems/birth-injuries>, retrieved Jan. 12, 2021 (6 pages).
UniProtKB—A0A0B6Z707, "Uncharacterized Protein—Arion Vulgaris," integrated into UniProtKB/TrEMBL on Apr. 1, 2015 (2 pages).
UniProtKB—A0A2J9MUW8, "PDGFC isoform 4—pan troglodytes (Chimpanzee)," integrated into UniProtKB/TrEMBL on Mar. 28, 2018 (5 pages).
UniProtKB—A0A2R6GW52, "Uncharaterized protein—*Halobacteriales archaeon* QS_6_64_34," integrated into UniProtKB/TrEMBL on Jun. 20, 2018 (3 pages).
Wasserman, M., "Involuntary Weight Loss," The Merck Manual, <https://www.merckmanuals.com/professional/special-subjects/nonspecific-symptoms/involuntary-weight-loss>, retrieved Jan. 12, 2021 (9 pages).

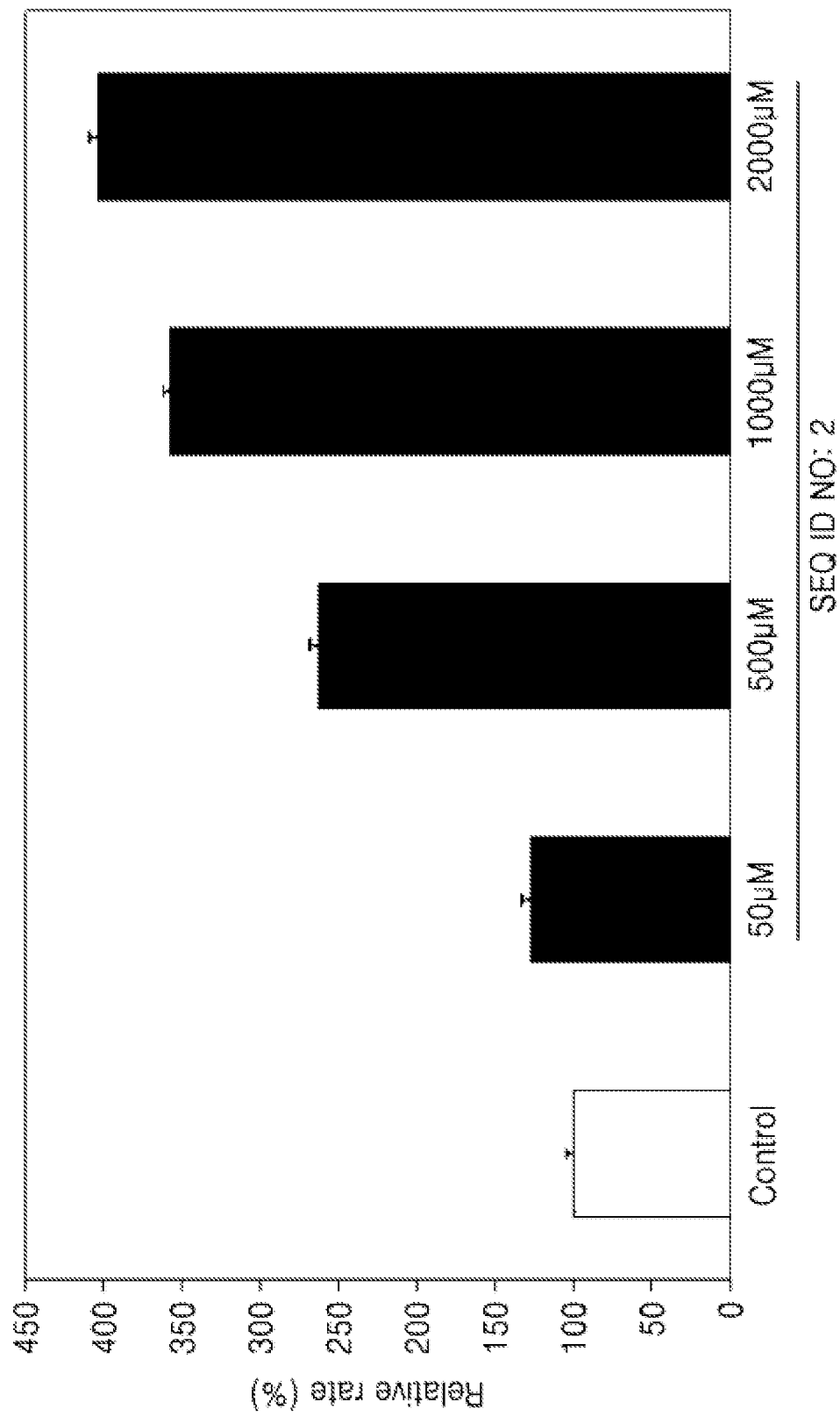

SEQUENCE LISTING

<160> NUMBER OF SEQ ID NOS: 13

<210> SEQ ID NO 1
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1

Lys Trp Gly Gly Gly Arg Tyr
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2

Ile Leu Gly Arg Trp Cys Gly
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic Construct

<400> SEQUENCE: 3

Asp Val Glu Asn Thr Ser
1               5

<210> SEQ ID NO 4
<211> LENGTH: 21
<212> TYPE: DNA
<213> ORGANISM: Artificial Sequence
<220> FEATURE:
<223> OTHER INFORMATION: Synthetic Construct

<400> SEQUENCE: 4
ggatctttct ctgtaccctg g                                              21

<210> SEQ ID NO 5
<211> LENGTH: 20
<212> TYPE: DNA
<213> ORGANISM: Artificial Sequence
<220> FEATURE:
<223> OTHER INFORMATION: Synthetic Construct

<400> SEQUENCE: 5
agcatgtcct tcagcccaga                                                20

<210> SEQ ID NO 6
<211> LENGTH: 21
<212> TYPE: DNA
<213> ORGANISM: Artificial Sequence
<220> FEATURE:
<223> OTHER INFORMATION: Synthetic Construct

<400> SEQUENCE: 6
cgtcagccga ttrtgctatc t                                              21

<210> SEQ ID NO 7
<211> LENGTH: 20
<212> TYPE: DNA
<213> ORGANISM: Artificial Sequence
<220> FEATURE:
<223> OTHER INFORMATION: Synthetic Construct

<400> SEQUENCE: 7
cggactccgc aaagtctaag                                                20

<210> SEQ ID NO 8
<211> LENGTH: 20
<212> TYPE: DNA
<213> ORGANISM: Artificial Sequence
<220> FEATURE:
<223> OTHER INFORMATION: Synthetic Construct

<400> SEQUENCE: 8
aaagaggcac tgccagaaaa                                                20

```
<210> SEQ ID NO 9
<211> LENGTH: 20
<212> TYPE: DNA
<213> ORGANISM: Artificial Sequence
<220> FEATURE:
<223> OTHER INFORMATION: Synthetic Construct

<400> SEQUENCE: 9
atctgaggtg cccatgctac                                              20

<210> SEQ ID NO 10
<211> LENGTH: 20
<212> TYPE: DNA
<213> ORGANISM: Artificial Sequence
<220> FEATURE:
<223> OTHER INFORMATION: Synthetic Construct

<400> SEQUENCE: 10
ttcgacacat gggataacga                                              20

<210> SEQ ID NO 11
<211> LENGTH: 20
<212> TYPE: DNA
<213> ORGANISM: Artificial Sequence
<220> FEATURE:
<223> OTHER INFORMATION: Synthetic Construct

<400> SEQUENCE: 11
tctttcaaca cgcaggacag                                              20

<210> SEQ ID NO 12
<211> LENGTH: 21
<212> TYPE: DNA
<213> ORGANISM: Artificial Sequence
<220> FEATURE:
<223> OTHER INFORMATION: Synthetic Construct

<400> SEQUENCE: 12
atcattcacc aggcaaattg c                                            21

<210> SEQ ID NO 13
<211> LENGTH: 21
<212> TYPE: DNA
<213> ORGANISM: Artificial Sequence
<220> FEATURE:
<223> OTHER INFORMATION: Synthetic Construct

<400> SEQUENCE: 13
ggcttcagca taaagcgttt g                                            21
```

PEPTIDE HAVING CYTOPROTECTIVE EFFECT AGAINST ENVIRONMENTAL POLLUTANT AND USE THEREOF

SEQUENCE LISTING

The instant application contains a Sequence Listing which has been submitted electronically in ASCII format and is hereby incorporated by reference in its entirety. Said ASCII copy, created on Jul. 28, 2021, is named 51401-01 4002_Sequence_Listing_7_28_21_ST25 and is 2,809 bytes in size.

TECHNICAL FIELD

The present disclosure relates to a peptide with a cytoprotective effect against environmental pollutants and a use thereof.

BACKGROUND ART

Environmental pollutants are classified as so-called endocrine disruptors, and types thereof include organochlorine substances such as dioxins, pesticides, phthalates, benzopyrenes, penta- to nonyl-phenols, bisphenol A, heavy metals, styrene dimers and trimers, and the like. These substances are chemically very stable and persist in the environment for a long time, and may reach the human body via the food chain due to a high degree of bioaccumulation.

Among them, dioxins commonly refer to chlorinated hydrocarbon compounds having similar chemical structures, i.e., polychlorinated dibenzo-p-dioxins (PCDDs) and polychlorinated dibenzofurans (PCDFs), and there are 75 different types of PCDD isomers and 135 different types of PCDF isomers according to the number of substituted chlorine atoms.

Dioxins are emitted or generated in the incineration of waste, in a bleaching process of paper or pulp, in the manufacture of plastics, in the manufacture of organochlorine pesticides, and the like. Because dioxins are colorless crystalline solids at room temperature, thermochemically stable, and easily soluble in fats, they are accumulated in fat tissues when introduced into living bodies. The effects thereof on human bodies may include reproductive dysfunction, miscarriage, abnormal fetal development, changes in hormonal regulatory function, development of diabetes, abnormal immune systems, damage to immune systems, possibility of causing cancer, and the like.

Fine dust is composed of sulfur dioxide, nitrogen oxides, lead, ozone, carbon monoxide, and the like. Fine dust having a particle diameter of 10 μm or less is referred to as coarse particulate matter (PM10). Ultrafine dust having a particle diameter of 2.5 μm or less is referred to as fine particulate matter (PM2.5). Fine dust may originate from either natural sources such as soil dust, sea salt, or plant pollen or from anthropogenic sources such as fumes generated when fossil fuels are burnt, vehicle exhaust gas, dust from construction sites, powdered raw materials and subsidiary materials in factories, and smoke from incineration facilities.

Such fine dust having a very small diameter of about 1/7 to 1/5 that of a human hair is inhaled deeply into the human body without being filtered while passing through the nasal cavity, oral cavity, and bronchial tubes. Fine dust introduced into the human body in a form in which it is adsorbed to the above-described toxic substances may cause inflammatory reactions of organs such as the airway, lungs, the cardiovascular system, and the brain, thereby inducing respiratory diseases and cardiovascular diseases. In October 2013, fine dust was classified as a Group 1 carcinogen by the International Agency for Research on Cancer under the World Health Organization.

Both dioxins and polycyclic aromatic hydrocarbons (PAH) contained in fine dust are known to penetrate into cells and activate the aryl hydrocarbon receptor (AhR). Via the activation mechanism of AhR, reactive oxygen species (ROS) increase in cells and a heterodimer complex of AhR and ARNT binds to a xenobiotic response element (XRE) increasing the expression of various inflammation mediators, microphthalmia-associated transcription factor (MITF), which is a melanin synthesis-related transcription factor, and matrix metalloproteinase (MMP), which is a wrinkle-generating enzyme. Thus, dermatitis, pigment hyperplasia (spots and freckles), wrinkles, and the like are caused in skin.

Previously available anti-pollutant products use raw materials that prevent adsorption of fine dust to skin or strengthen the skin barrier using electric charges. However, from this, only indirect protective effects are obtained, instead of direct inhibition of the activation mechanisms of environment pollutants such as dioxins or fine dust. Raw materials or products inhibiting adverse effects of environmental pollutants in contact with skin have not been developed.

DESCRIPTION OF EMBODIMENTS

Technical Problem

Accordingly, the present inventors found that a peptide consisting of an amino acid sequence of SEQ ID NO: 1, 2, or 3 directly binds to 2,3,7,8-tetrachlorodibenzo-p-dioxin (hereinafter, referred to as TCDD), known as being the most toxic among the class of dioxins, acting to prevent dermal penetration thereof and the activation mechanism of the aryl hydrocarbon receptor (AhR) by TCDD and polycyclic aromatic hydrocarbons contained in fine dust.

Thus, an object of the present disclosure is to provide a peptide consisting of an amino acid sequence of SEQ ID NO: 1, 2, or 3.

Another object of the present disclosure is to provide a pharmaceutical composition for preventing or treating diseases caused by dioxin-like substances, the pharmaceutical composition including at least one peptide selected from the group consisting of peptides consisting of an amino acid sequence of SEQ ID NO: 1, 2, or 3.

Another object of the present disclosure is to provide a food composition for alleviating and/or ameliorating diseases caused by dioxin-like substances, the food composition including at least one peptide selected from the group consisting of peptides consisting of an amino acid sequence of SEQ ID NO: 1, 2, or 3 as an active ingredient.

Another object of the present disclosure is to provide a cosmetic composition for improving skin condition including at least one peptide selected from the group consisting of peptides consisting of an amino acid sequence of SEQ ID NO: 1, 2, or 3 as an active ingredient.

Another object of the present disclosure is to provide a method of preventing or treating diseases caused by dioxin-like substances.

Another object of the present disclosure is to provide a use of a peptide consisting of an amino acid sequence of SEQ ID NO: 1, 2, or 3 for preventing or treating diseases caused by dioxin-like substances.

Solution to Problem

The present disclosure relates to a peptide with a cytoprotective effect against environmental pollutants and a use thereof. It has been confirmed that a peptide consisting of an amino acid sequence of SEQ ID NO: 1, 2, or 3 directly binds to 2,3,7,8-tetrachlorodibenzo-p-dioxin (hereinafter, referred to as TCDD), known as being the most toxic among the class of dioxins, acting to prevent dermal penetration thereof and the activation mechanism of aryl hydrocarbon receptors (AhR) by TCDD and polycyclic aromatic hydrocarbons contained in fine dust. Such a direct cytoprotective effect against environmental pollutants is distinguished from pre-existing methods that are configured to indirectly block the opportunity to contact these materials or to reduce toxicity through barrier enforcement.

Hereinafter, the present disclosure will be described in more detail.

In an aspect of the present disclosure, provided is a peptide consisting of an amino acid sequence of SEQ ID NO: 1, 2, or 3.

The peptide may be one in which N-terminal and/or C-terminal modification is induced to select a portion of the amino acid sequence and increase the activity thereof. Such N-terminal and/or C-terminal modification may considerably improve stability of the peptide according to the present disclosure, for example, increase half-life of in vivo administration of the peptide.

The N-terminal modification may be obtained by binding a protective group selected from the group consisting of an acetyl group, a fluoreonylmethoxycarbonyl group, a formyl group, a palmitoyl group, a myristyl group, a stearyl group, and a polyethylene glycol (PEG) to the N-terminal of the peptide. The protective group acts to protect the peptide of the present disclosure from attacks of a protein cleaving enzyme in a living body.

The C-terminal modification may be obtained by binding a hydroxyl group (—OH), an amino group (—NH$_2$), an azide group (—NHNH$_2$), or the like to the C-terminal of the peptide, without being limited thereto.

According to an embodiment, the peptide consisting of an amino acid sequence of SEQ ID NO: 1, 2, or 3 directly binds to 2,3,7,8-tetrachlorodibenzo-p-dioxin (hereinafter, referred to as TCDD), known as being the most toxic among the class of dioxins, having effects of preventing dermal penetration thereof and the activation mechanism of AhR by TCDD and polycyclic aromatic hydrocarbons contained in fine dust.

Polycyclic aromatic hydrocarbon introduced into a cell binds to the AhR and moves into the nucleus, and then forms a complex with AhR nuclear translocator (ARNT) which binds to a dioxin-responsive element (DRE) to induce expression of downstream genes. The downstream genes include CYP1A1 and various inflammatory factors. CYP1A1 is involved in metabolisms of various carcinogenic precursors such as benzopyrene, and metabolites generated therefrom react with DNA to cause mutation. Also, expressions of inflammatory factors such as cyclooxygenase 2 (COX2), tumor necrosis factor alpha (TNF-a), and interleukin-1 beta (IL-1b) are increased, resulting in inflammation reactions locally on a contact region and systemically.

These results indicate that the peptide of the present disclosure has excellent effects on prevention and/or treatment of diseases caused by dioxin-like substances.

In another aspect of the present disclosure, provided is a pharmaceutical composition for preventing or treating diseases caused by dioxin-like substances including at least one peptide selected from the group consisting of peptides consisting of an amino acid sequence of SEQ ID NO: 1, 2, or 3.

The diseases caused by dioxin-like substances are very complex and examples thereof include, but are not limited to, skin diseases including chloracne, decreased sperm count, testicular cancer, prostate cancer, endometrial hyperplasia, breast cancer, hepatotoxicity, weakened immunity, hyperlipidemia, hypospadia, cryptorchidism, deformed child birth, injury of blood vessel, hepatocellular carcinoma, hepatomegaly, adenofibrosis, weight loss, hair loss, oral edema, blepharedema, and gastric mucosal ulcer (Carter et al., Science 188:738 (1975); Fourth Annual Report on Carcinogens, NTP 85-002:170, 185 (1985)).

As used herein, the term "dioxin", commonly used in mass media, is used as a shortened word of 2,3,7,8-tetrachlorodibenzo-p-dioxin (hereinafter, referred to as TCDD). However, TCDD is a member of the polychlorinated dibenzo-p-dioxin family (hereinafter, PCDD), and PCDDs include 75 different types of congeners according to positions and numbers of chlorine atoms. Biologically, TCDD is known as the most toxic PCDD.

Meanwhile, other aromatic hydrocarbons having the same biological characteristics as those of TCDDs, e.g., the polychlorinated dibenzofuran family (PCDFs) and the polychlorinated biphenyl family (PCBs), have been reported.

Thus, the term "dioxin" as used herein refers to all compounds included in PCDDs, and the term "dioxin-like substances" include PCDDs, PCDFs, and PCBs described above and refer to substances having the same cellular effects as those of PCDDs.

Dioxin, as a carcinogenic substance, has been reported to cause serious diseases such as disturbance of reproductive and developmental processes, impairment of the immune system, and interference of hormonal regulation (Yang, J. H. et al., Carcinogenesis. 20: 13-18(1999), Lee, Y. W. et al., Toxicol. Lett., 102-103:29-83(1998)).

The United States Environmental Protection Agency (EPA) has collected statistic data on adverse effects of dioxin and dioxin-like substances on human bodies and reported that the sperm count decrease by about 50%, occurrences of testicular cancer increase by approximately 3 times, and occurrences of prostate cancer increase by twice or more, when compared with those 50 years ago. In addition, increases in occurrences of endometrial hyperplasia and breast cancer caused by dioxin and the like have been confirmed when compared those in the past.

The pharmaceutical composition may include a pharmaceutically effective amount of the at least one peptide selected from the group consisting of peptides consisting of an amino acid sequence of SEQ ID NO: 1, 2, or 3.

Also, the pharmaceutical composition may further include a pharmaceutically acceptable carrier.

The pharmaceutically acceptable carrier may be any substance commonly used in pharmaceutical preparations and examples thereof include, but are not limited to, lactose, dextrose, sucrose, sorbitol, mannitol, starch, acacia rubber, calcium phosphate, alginate, gelatin, calcium silicate, microcrystalline cellulose, polyvinyl pyrrolidone, cellulose, water, syrup, methylcellulose, methylhydroxy benzoate, propylhydroxy benzoate, talc, magnesium stearate, and mineral oil Suitable pharmaceutically acceptable carriers and preparations are described in Remington's Pharmaceutical Sciences (19th ed., 1995) in detail.

The pharmaceutical composition according to the present disclosure may further include, but is not limited thereto, a lubricant, a wetting agent, a sweetener, a flavor, an emulsifier, a suspension, and a preservative in addition to the ingredients.

The pharmaceutical composition may be administered orally or parenterally, preferably, parenterally. When parenterally administered, intramuscular injection, intravenous injection, subcutaneous injection, intraperitoneal injection, local administration, transdermal administration, and the like may be used, without being limited thereto.

Dosage of the pharmaceutical composition may be, but is not limited to, in the range of 0.0001 µg to 1000 µg, 0.001 µg to 1000 µg, 0.01 µg to 1000 µg, 0.1 µg to 1000 µg, or 1.0 µg 1000 µg, per day and may be variously prescribed according to factors such as formulating method, administration method, age, weight, gender, and pathological condition of a patient, food, administration time, administration route, excretion rate, and reaction sensitivity.

The pharmaceutical composition may be formulated into a unit dosage form or a multiple dosage form using a pharmaceutically acceptable carrier and/or an excipient by a well-known method in the art.

The formulation may be a solution in oil or an aqueous medium, a suspension, an emulsion, an extract, powder, granules, a tablet, or a capsule, and may further include a dispersant or a stabilizer.

In another aspect of the present disclosure, provided is a food composition antagonistic to dioxin-like substances including at least one peptide selected from the group consisting of peptides consisting of an amino acid sequence of SEQ ID NO: 1, 2, or 3 as an active ingredient.

In another aspect of the present disclosure, provided is a food composition for alleviating and/or ameliorating diseases caused by dioxin-like substances including at least one peptide selected from the group consisting of peptides consisting of an amino acid sequence of SEQ ID NO: 1, 2, or 3 as an active ingredient.

The diseases caused by dioxin-like substances may include, but are not limited to, decreased sperm count, testicular cancer, prostate cancer, endometrial hyperplasia, breast cancer, hepatotoxicity, weakened immunity, hyperlipidemia, hypospadia, cryptorchidism, deformed child birth, injury of blood vessel, hepatocellular carcinoma, hepatomegaly, adenofibrosis, weight loss, hair loss, oral edema, blepharedema, and gastric mucosal ulcer.

The food may be various foods, beverages, food additives, and the like.

An amount of the peptide, as an active ingredient, contained in the food composition, is not particularly limited and may be appropriately adjusted according to types of food, purposes thereof, and the like, for example, in the range of 0.01 wt % to 15 wt % based on a total weight of a food or in the range of 0.02 g to 10 g, preferably, 0.3 g to 1 g, based on 100 ml of a functional beverage composition.

When the food is a beverage, liquid ingredients are not particularly limited so long as the peptide is contained as an essential ingredient in a given ratio. The beverage may further include additional ingredients such as various flavors or natural carbohydrates.

Examples of the natural carbohydrates include conventional sweeteners, for example, monosaccharides such as glucose and fructose, disaccharides such as maltose and sucrose, and polysaccharides such as dextrin and cyclodextrin, and sugar alcohol such as xylitol, sorbitol, and erythritol.

In addition to those described above, natural flavors (e.g., thaumatin and stevia extract, e.g., rebaudioside A and glycyrrhizin) and synthetic flavors (e.d., saccharin and aspartame) may be efficiently used as the flavor. An amount of the natural carbohydrates may be in the range of about 1 g to about 20 g, preferably about 5 g to about 12 g, based on 100 ml of the composition according to the present disclosure.

The food composition of the present disclosure may further include nutrients, vitamins, minerals, flavors such as synthetic flavors and natural flavors, colorants, and extenders (cheese, chocolate, etc.), pectic acid and salts thereof, alginic acid and salts thereof, organic acid, protective colloidal thickeners, pH controllers, stabilizers, preservatives, glycerin, alcohol, and carbonating agents used in carbonated beverages.

The food composition of the present disclosure may further include fruit flesh for preparing natural fruit juices, fruit juice beverages, and vegetable beverages. These ingredients may be used independently or in combinations. The amounts of the additives are not important, but may be in the range of the weight ratio of 0 to about 20 parts by weight based on 100 parts by weight of the composition according to the present disclosure.

In another aspect of the present disclosure, provided is a cosmetic composition for improving skin conditions including at least one peptide selected from the group consisting of peptides consisting of an amino acid sequence of SEQ ID NO: 1, 2, or 3.

The cosmetic composition may include (a) a cosmetically effective amount of the peptide according to the present disclosure described above, and/or (b) a cosmetically acceptive carrier, without being limited thereto.

As used herein, the term "cosmetically effective amount" refers to an amount sufficient to achieve the effect of the composition according to the present disclosure on improving skin conditions.

The cosmetic composition may be prepared into any formulation commonly used in the art. For example, the cosmetic composition may be formulated into, but is not limited to, solution, suspension, emulsion, paste, gel, cream, lotion, powder, soap, surfactant-containing cleanser, oil, powdered foundation, emulsion foundation, wax foundation, and spray. More particularly, the cosmetic composition may be formulated into emollient lotion, nourishing lotion, nourishing cream, massage cream, essence, eye cream, cleansing cream, cleansing foam, cleansing water, pack, spray, or powder.

When the cosmetic composition of the present disclosure is formulated into paste, cream, or gel, the carrier may be animal oil, plant oil, wax, paraffin, starch, tragacanth, cellulose derivatives, polyethylene glycol, silicone, bentonite, silica, talc, zinc oxide, or the like.

When the cosmetic composition of the present disclosure is formulated into powder or spray, the carrier may be lactose, talc, silica, aluminum hydroxide, calcium silicate, or polyamide powder. Particularly, in the form of spray, a propellant such as chlorofluorohydrocarbon, propane/butane, or dimethyl ether may further be used.

When the cosmetic composition of the present disclosure is formulated into solution or emulsion, the carrier may be a solvent, a solubilizer, or emulsifier, such as water, ethanol, isopropanol, ethyl carbonate, ethyl acetate, benzyl alcohol, benzyl benzoate, propylene glycol, 1,3-butylglycol oil, glycerol aliphatic ester, polyethylene glycol, or fatty acid ester of sorbitan.

When the cosmetic composition of the present disclosure is formulated into suspension, the carrier may be a liquid diluent such as water, ethanol, or propylene glycol, a suspending agent such as ethoxylated isostearyl alcohol, polyoxyethylene sorbitol ester, and polyoxyethylene sorbitan ester, microcrystalline cellulose, aluminum metahydroxide, bentonite, agar, and tragacanth.

When the cosmetic composition of the present disclosure is formulated into the surfactant-containing cleanser, the carrier may be aliphatic alcohol sulfate, aliphatic alcohol ether sulfate, sulfosuccinic monoester, isethionate, imidazolinium derivatives, methyl taurate, sarcosinate, fatty acid amide ether sulfate, alkyl amidobetaine, aliphatic alcohol, fatty acid glyceride, fatty acid diethanolamide, vegetable oil, lanolin derivatives, or ethoxylated glycerol fatty acid ester.

The cosmetic composition according to the present disclosure may further include, in addition to the peptide and the carrier as the active ingredients, other components commonly used in cosmetic compositions. For example, common adjuvants such as an antioxidant, a stabilizer, a solubilizer, vitamins, pigment, and fragrance may be included therein.

As used herein, the term "improvement of skin conditions" widely indicates processes of treating, relieving, and alleviating damage of skin caused by an intrinsic or extrinsic factor, and effects thereof, for example, may be interpreted as showing the effect of alleviating or ameliorating inflammation occurring in skin, but is not limited thereto.

In another aspect of the present disclosure, provided is a method of preventing of treating diseases caused by dioxin-like substances.

The method may include brining a pharmaceutical composition including at least one peptide selected from peptides consisting of an amino acid sequence of SEQ ID NO: 1, 2, or 3, into contact with a subject.

The pharmaceutical composition is as described above.

In another aspect of the present disclosure, provided is a use of a peptide consisting of an amino acid sequence of SEQ ID NO: 1, 2, or 3 for preventing or treating diseases caused by dioxin-like substances.

The peptide consisting of an amino acid sequence of SEQ ID NO: 1, 2, or 3 is as described above.

Throughout the specification, the term "peptide" refers to a linear molecule composed of amino acid residues linked via peptide bonds. The peptide according to the present disclosure may be prepared according to any known chemical synthesis methods, particularly, solid-phase synthesis techniques (Merrifield, J. Amer. Chem. Soc. 85:2149-54 (1963); Stewart, et al., Solid Phase Peptide Synthesis, 2nd. ed., Pierce Chem. Co.: Rockford, 111(1984)) or liquid-phase synthesis techniques (U.S. Pat. No. 5,516,891).

As used herein, the term "stability" refers to not only in vivo stability but also storage stability (e.g., storage stability at room temperature).

Throughout the specification, the term "pharmaceutical effective amount" refers to an amount sufficient to achieve the effect or activity of the peptide.

Advantageous Effects of Disclosure

The present disclosure relates to a peptide with a cytoprotective effect against environmental pollutants and a use thereof. It was confirmed that a peptide consisting of an amino acid sequence of SEQ ID NO: 1, 2, or 3 directly binds to 2,3,7,8-tetrachlorodibenzo-p-dioxin (hereinafter, referred to as TCDD), known as being the most toxic among the class of dioxins, acting to prevent dermal penetration thereof and the activation mechanism of the aryl hydrocarbon receptor (AhR) by TCDD and polycyclic aromatic hydrocarbons contained in fine dust. Such a direct cytoprotective effect against environmental pollutants is distinguished from pre-existing methods that are configured to indirectly block opportunities to contact these materials or to reduce toxicity through barrier reinforcement.

BRIEF DESCRIPTION OF DRAWINGS

FIG. 1B is a graph showing binding strength of a peptide consisting of an amino acid sequence of SEQ ID NO: 2 to TCDD, according to an embodiment of the present disclosure.

BEST MODE

Figure 1A:
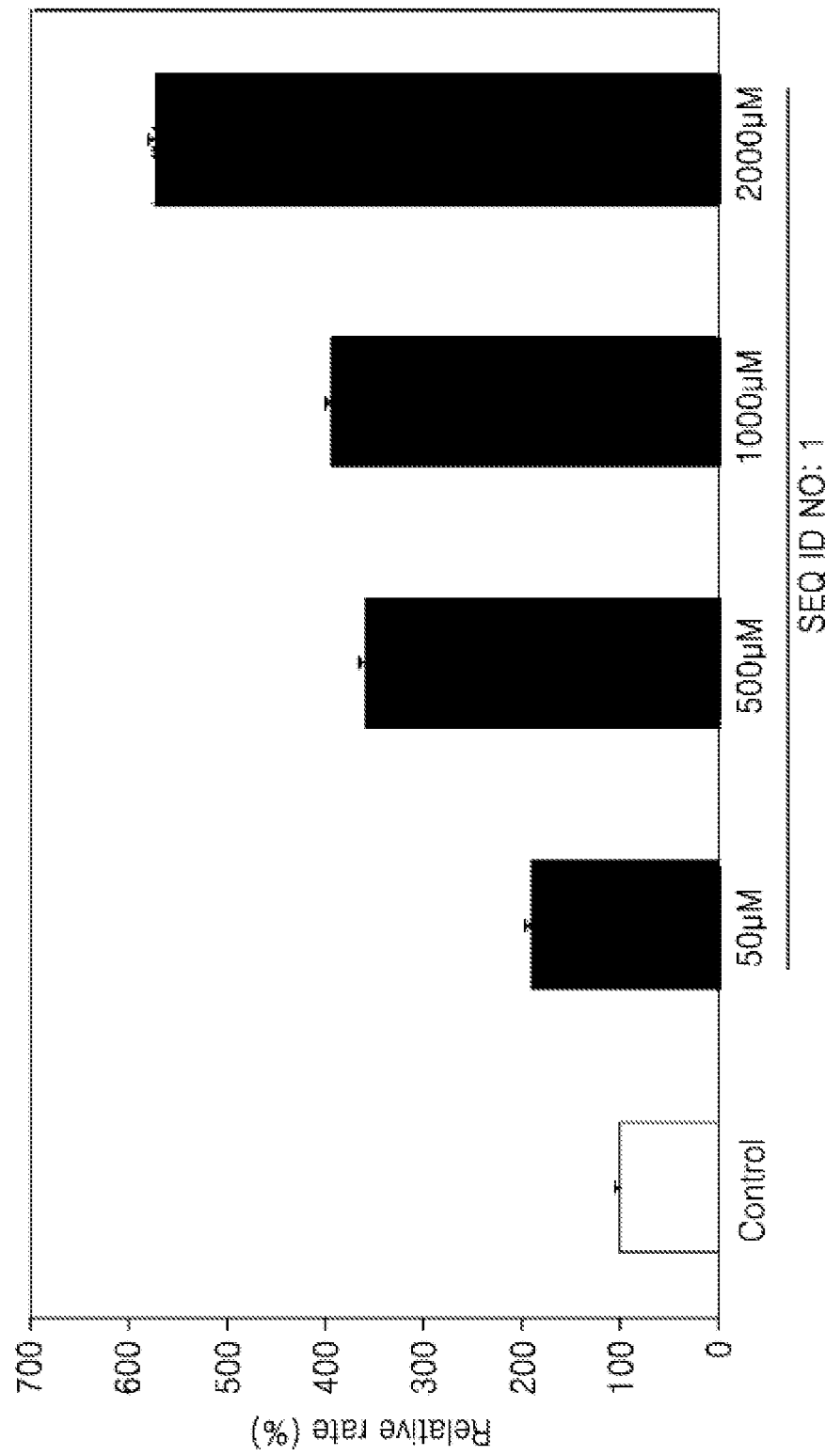
FIG. 1A is a graph showing binding strength of a peptide consisting of an amino acid sequence of SEQ ID NO: 1 to TCDD, according to an embodiment of the present disclosure.

The present disclosure relates to a peptide consisting of an amino acid sequence of SEQ ID NO: 1, 2, or 3.

MODE OF DISCLOSURE

Hereinafter, the present disclosure will be described in more detail with reference to the following examples. However, these examples are for illustrative purposes only and are not intended to limit the scope of the present disclosure.

Preparation Example. Synthesis of Sequence List 70 g of chloro trityl chloride resin (CTC resin, Nova biochem Cat No. 01-64-0021) was added to a reactor and 490 ml of methylene chloride (MC) was added thereto, followed by stirring for 3 minutes. Subsequently, after the solution was removed therefrom, 490 ml of dimethyl formamide (DMF) was added thereto, the mixture was stirred for 3 minutes, and the solvent was removed therefrom. 700 ml of dichloromethane solution was added to the reactor, and then 200 mmole of Fmoc-Tyr(tBu)-OH (Bachem, Swiss) and 400 mmole of diisopropyl ethylamine (DIEA) were added thereto. The mixture was dissolved by stirring and maintained for 1 hour while stirring. After the resultant was washed, methanol and DIEA (2:1) were dissolved in dichloromethane (DCM) and maintained for 10 minutes, and then the resultant was washed with an excess of DCM/DMF (1:1). Then, after the solution was removed, 490 ml of dimethyl formamide (DMF) was added thereto, and the mixture was stirred for 3 minutes, and then the solvent was removed therefrom. 700 ml of a deprotection solution (20% piperidine/DMF) was added to the reactor and stirred for 10 minutes at room temperature, and then the solution was removed. After the same amount of the deprotection solution was added thereto and maintained for 10 minutes, the solution was removed and the resultant was washed twice with DMF, once with MC, and once with DMF, each for 3 minutes to prepare a Tyr(tBu)-CTL resin.

700 ml of a DMF solution was added to a new reactor, and 200 mmole of Fmoc-Arg(Pbf)-OH (Bachem, Swiss), 200 mmole of HoBt, and 200 mmole of HBTu were added thereto and dissolved by stirring. 400 mmole of DIEA was added to the reactor in twice and the mixture was stirred for at least 5 minutes to completely dissolve all solids. The dissolved amino acid mixture solution was added to the reactor including the deprotected resin and maintained for 1 hour at room temperature while stirring. After the reaction solution was removed, the resultant was stirred with a DMF solution three times each for 5 minutes and then the DMF solution was removed therefrom. A small amount of the reaction resin was taken and the degree of reaction was checked by Kaiser test (Nihydrin Test). Deprotection reaction was conducted twice in the same manner using the deprotection solution to prepare an Arg(Pbf)-Tyr(tBu)-CTL resin. The resin was sufficiently washed with DMF and MC and subjected to the Kaiser test again, followed by amino acid binding test as describe above. According to a selected amino acid sequence, chain reactions were conducted in the order of Fmoc-Gly-OH, Fmoc-Gly-OH, Fmoc-Gly-OH, Fmoc-Trp-OH, and Fmoc-Lys(Boc)-OH. After the Fmoc-protective group was reacted with the deprotection solution twice each for 10 minutes, the deprotection solution was removed by washing. The peptidyl resin was washed with DMF, MC, and methanol three times each, and dried while slowly flowing nitrogen gas, and then completely dried under the $P_2O_5$ atmosphere in a vacuum. Then, 1,900 ml of a leaving solution [81.5% of trifluroacetic acid, 5.0% of distilled water, 5.0% of thioanisole, 5.0% of phenol, 2.5% of ethanedithiol (EDT), and 1.0 5 of triisopropylsilane (TIS)] was added thereto, and reactions of the mixture were maintained at room temperature for 2 hours while shaking. The resin was filtered, washed with a small amount of a TFA solution, and mixed with a mother solution. Cold ether was added to 2,090 ml of the mother solution to induce precipitation, and the mixture was centrifuged to collect precipitates, and then washed twice with cold ether. After removing the mother solution, the resultant was sufficiently dried under a nitrogen atmosphere to synthesize 70.8 g of a peptide consisting of an amino acid sequence of SEQ ID NO: 1 before purification (Yield: 97.0%). A molecular weight of 822.9 (Theoretical value: 822.9) was obtained using a molecular weight measurer.

Peptides having amino acid sequences of SEQ ID NO: 2 or SEQ ID NO: 3 are synthesized in the same manner as the above method.

TABLE 1

| SEQ ID NO: | Sequence list | Analysis value (mass spectrometer) | |
|---|---|---|---|
| | | Obtained value | Theoretical value |
| 1 | KWGGGRY | 822.9 | 822.9 |
| 2 | ILGRWCG | 803.9 | 803.9 |
| 3 | DVENTS | 663.6 | 663.6 |

Example 1. In Vitro Binding Assay

Each of the peptides having amino acid sequences of SEQ ID NOS: 1, 2, and 3 mixed with a coating buffer (20 mM sodium phosphate, pH 9.6) at a concentration of 1.8 mM was seeded on a plate for an enzyme-linked immunosorbent assay (ELISA) and cultured at 4° C. overnight. Subsequently, the peptide was washed with phosphate buffered saline with Tween-20 (PBST) and blocked with 3% of bovine serum albumin (BSA) for 2 hours at room temperature. After washing with PBST, 2 µM of 2,3,7,8-tetrachlorodibenzo-p-dioxin (hereinafter, referred to as TCDD) was added to each well and cultured at room temperature for 2 hours. Subsequently, after washing with PBST, treatment with anti-TCDD antibody conjugated with fluorescein isothiocyanate (FITC) was conducted at a ratio of antibody:PBST=1:100 and the resultant was cultured for 2 hours at room temperature. Then, after washing with PBST, an excitation 488 nm/emission 520 nm value was measured using a fluorescence meter, and the results are shown in FIGS. 1A to 1C, and Table 2.

TABLE 2

| SEQ ID NO: | Control | 50 µM | 500 µM | 1000 µM | 2000 µM |
|---|---|---|---|---|---|
| 1 | 100% | 193% | 360% | 394% | 575% |
| 2 | 100% | 128% | 264% | 358% | 405% |
| 3 | 100% | 159% | 253% | 400% | 420% |

Figure 1C:
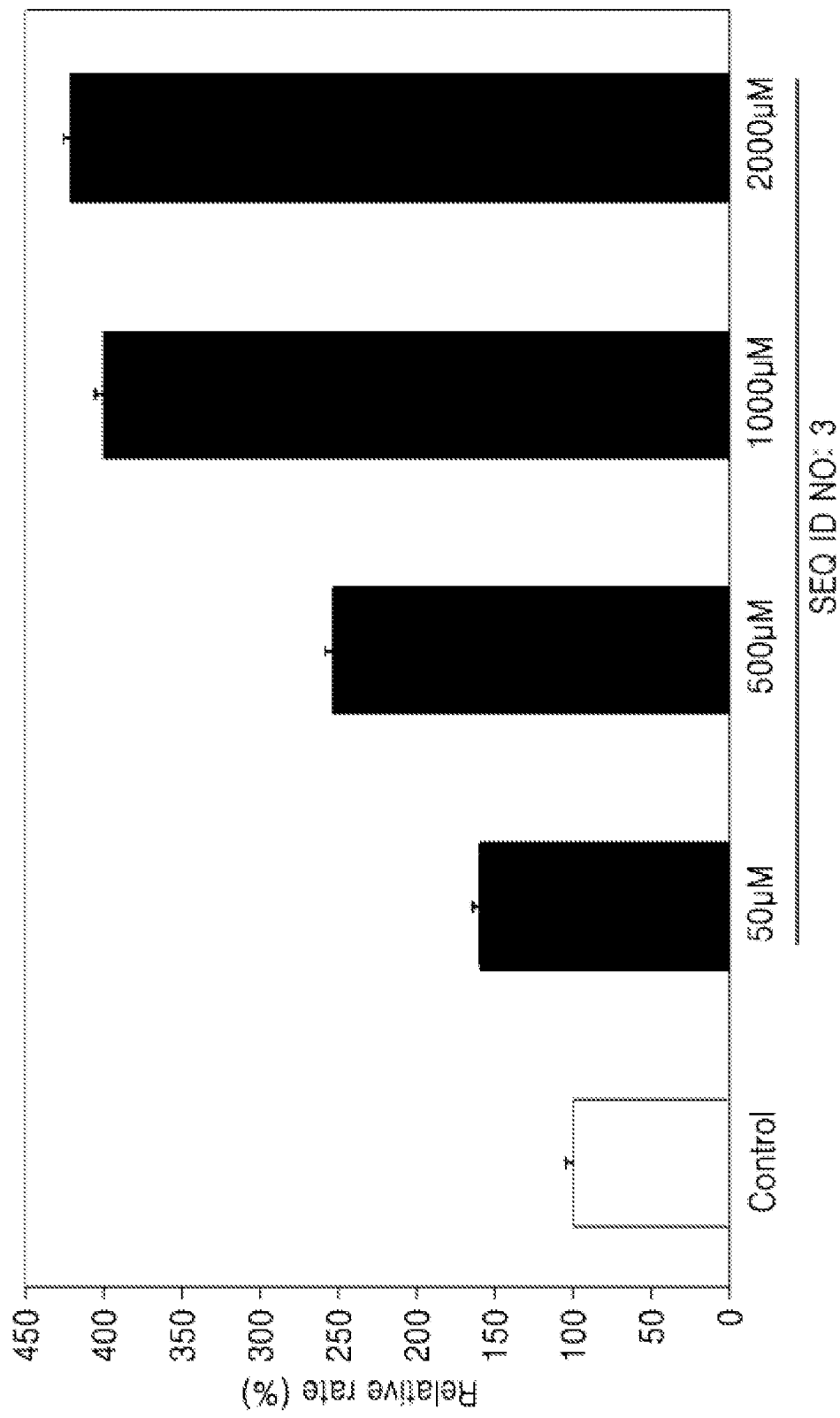
FIG. 1C is a graph showing binding strength of a peptide consisting of an amino acid sequence of SEQ ID NO: 3 to TCDD, according to an embodiment of the present disclosure.
Figure 2A:
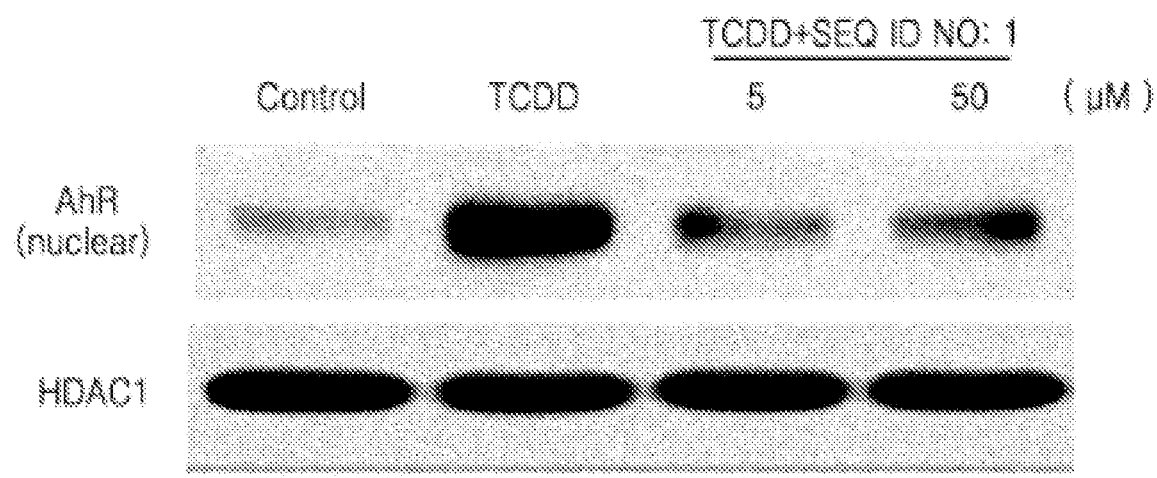
FIG. 2A shows AhR nuclear translocation test results of a peptide consisting of an amino acid sequence of SEQ ID NO: 1 according to an embodiment of the present disclosure.
Figure 2B:
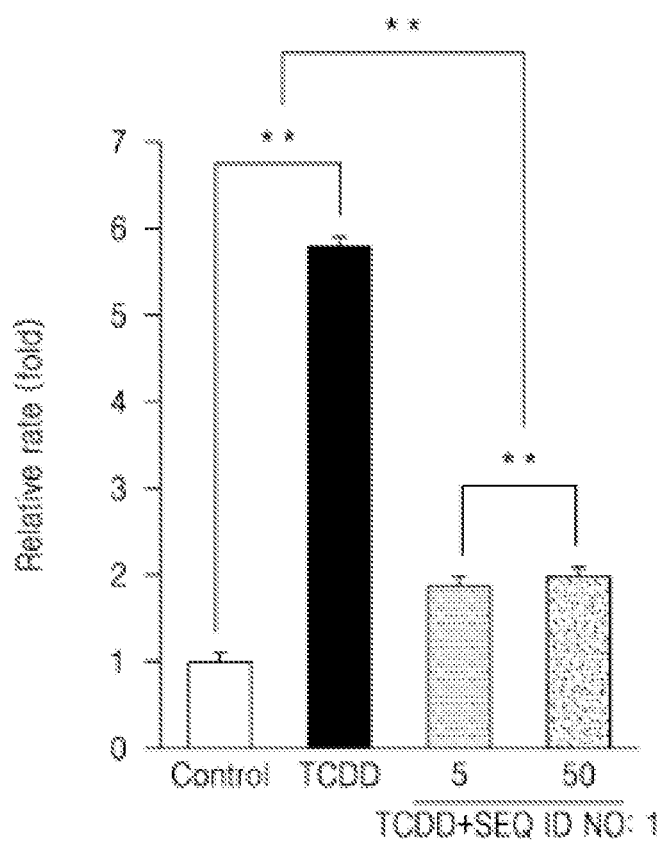
FIG. 2B is a graph showing AhR nuclear translocation test results of the peptide consisting of an amino acid sequence of SEQ ID NO: 1 according to an embodiment of the present disclosure.
Figure 2C:
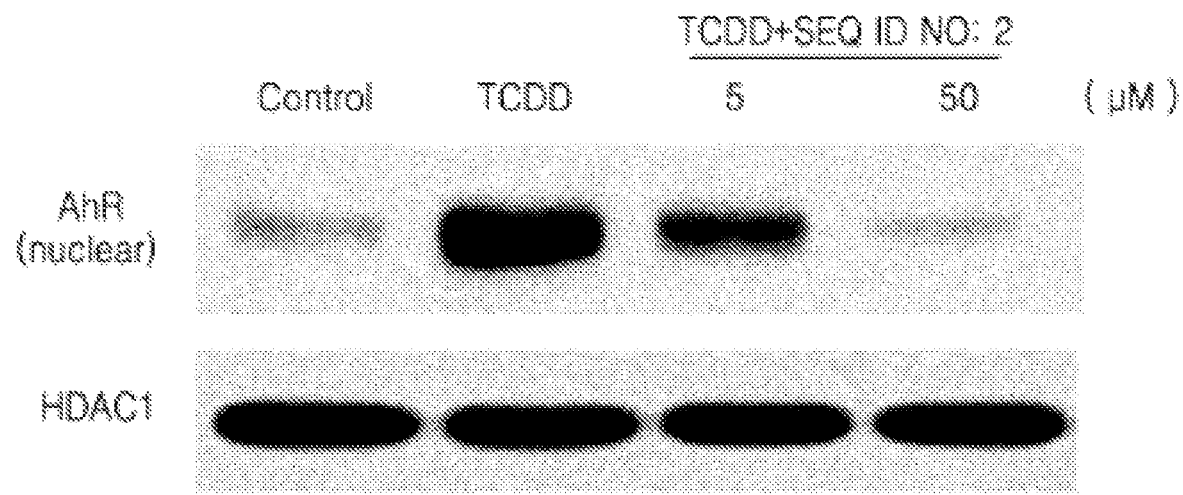
FIG. 2C shows AhR nuclear translocation test results of a peptide consisting of an amino acid sequence of SEQ ID NO: 2 according to an embodiment of the present disclosure.
Figure 2D:
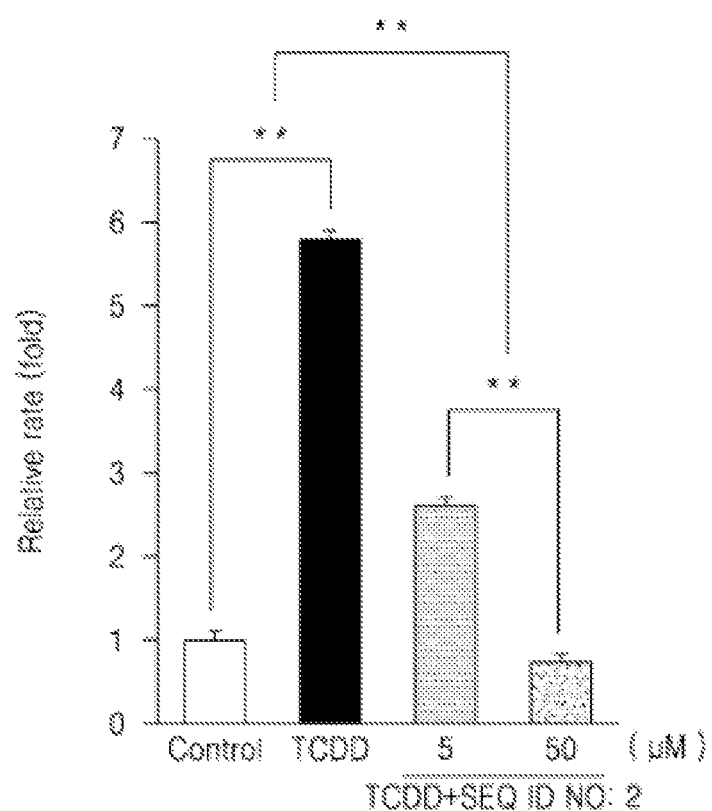
FIG. 2D is a graph showing AhR nuclear translocation test results of the peptide consisting of an amino acid sequence of SEQ ID NO: 2 according to an embodiment of the present disclosure.
Figure 2E:
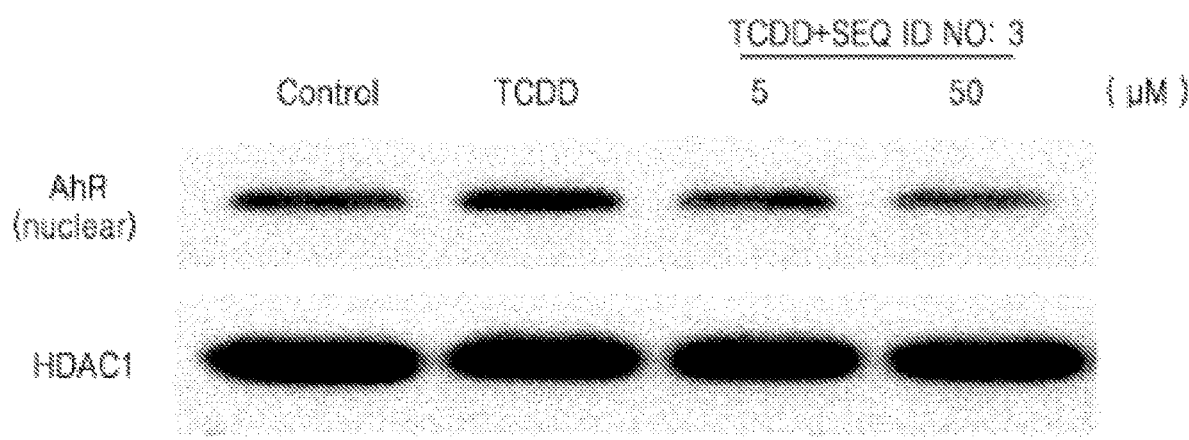
FIG. 2E shows AhR nuclear translocation test results of a peptide consisting of an amino acid sequence of SEQ ID NO: 3 according to an embodiment of the present disclosure.
Figure 2F:
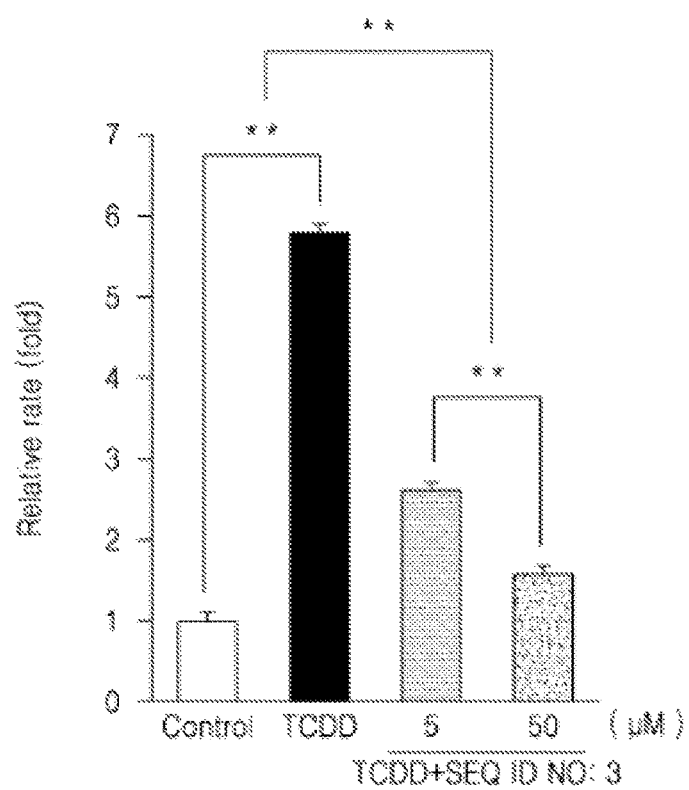
FIG. 2F is a graph showing AhR nuclear translocation test results of the peptide consisting of an amino acid sequence of SEQ ID NO: 3 according to an embodiment of the present disclosure.

As shown in FIGS. 1A to 1C and Table 2, it was confirmed that the peptide consisting of an amino acid sequence of SEQ ID NO: 1, 2, or 3 directly binds to TCDD.

Example 2. AhR Nuclear Translocation Test

HaCaT cells, human keratinocyte cells, were seeded on a 6-well plate at a density of $3 \times 10^5$ cells/well and cultured overnight. Subsequently, 10 nM of TCDD and 50 µM of the peptide consisting of an amino acid sequence of SEQ ID NO: 1, 2, or 3 were added to the culture medium. After 30 minutes of reaction, the cells were treated for 1 hour and collected to obtain nuclei and cytoplasmic proteins separated from each other. Westin blotting was performed using an aryl hydrocarbon receptor (AhR) antibody (Santa Cruz Biotechnology, U.S.A.) to identify activated nuclear translocation of AhR, and the results are shown in FIGS. 2A to 2F and Table 3.

TABLE 3

| | | | TCDD + Peptide | |
|---|---|---|---|---|
| SEQ ID NO: | Control | TCDD | 5 µM | 50 µM |
| 1 | 1 times | 5.8 times | 1.9 times | 1.9 times |
| 2 | 1 times | 5.7 times | 2.5 times | 0.9 times |
| 3 | 1 times | 5.9 times | 3 times | 1.5 times |

As shown in FIGS. 2A to 2F and Table 3, it was confirmed that the peptide consisting of an amino acid sequence of SEQ ID NO: 1, 2, or 3 inhibits nuclear translocation of AhR by TCDD.

Example 3. TCDD ICC

HaCaT cells, human keratinocyte cells, were seeded on a 6-well plate at a density of $3 \times 10^5$ cells/well and cultured overnight. Subsequently, 50 nM of TCDD and 50 µM of the peptide consisting of an amino acid sequence of SEQ ID NO: 1, 2, or 3 were added to the culture medium. After 30 minutes of reaction, the cells were treated for 5 minutes and immobilized with 4% paraformaldehyde for 30 minutes. Then, after washing three times, the cells were reacted with 0.5% Triton X-100 for 15 minutes and washed three times. Subsequently, the cells were blocked with 3% BSA for 1 hour and reacted with a primary antibody against TCDD conjugated with fluorescein isothiocyanate (FITC) (1:100) at 4° C. overnight. The cells were stained and mounted with 4,6-diamidino-2-phenylindole (DAPI) and observed with a fluorescence microscope. The results are shown in FIGS. 3A to 3C.

Figure 3A:
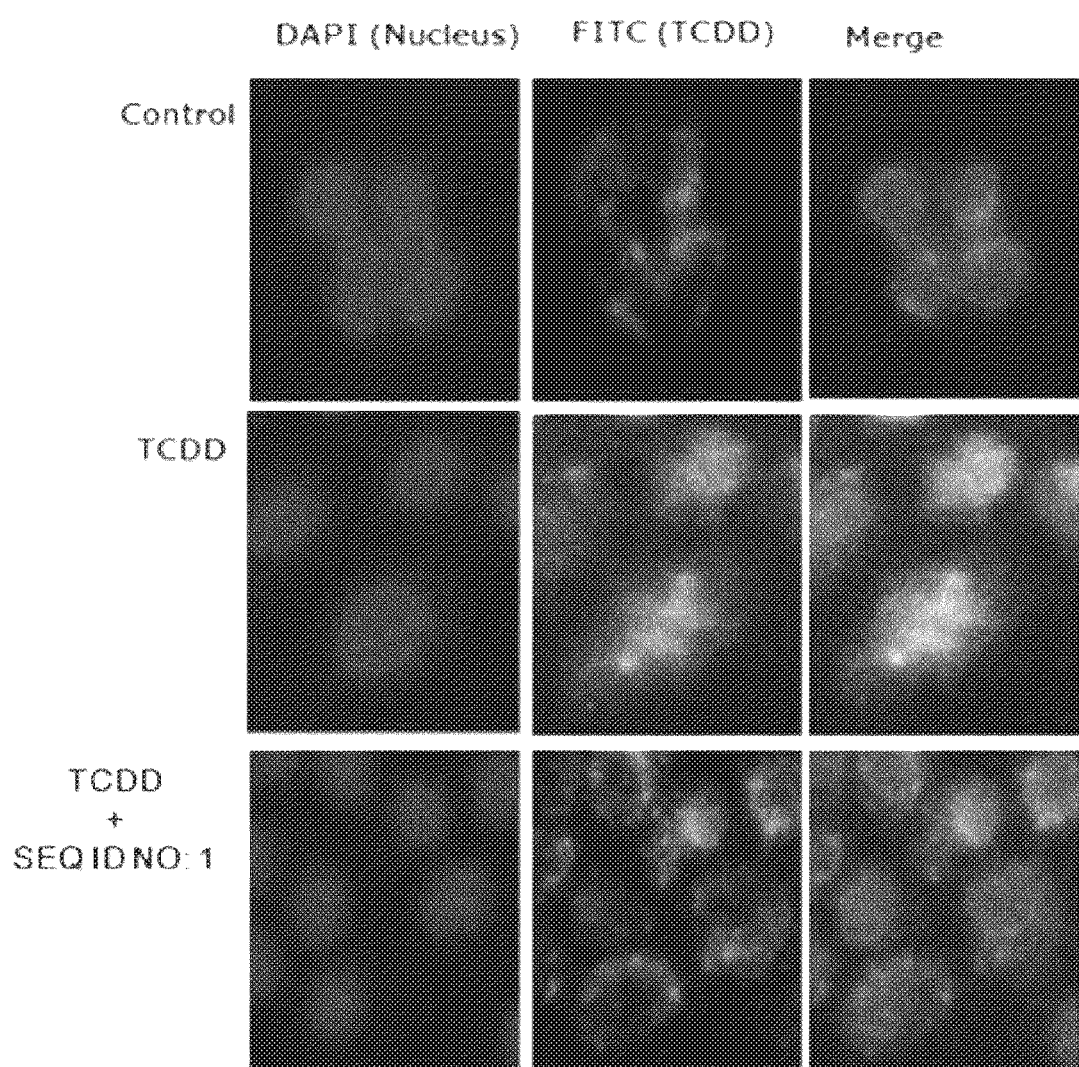
FIG. 3A is a graph showing TCDD ICC results of a peptide consisting of an amino acid sequence of SEQ ID NO: 1 according to an embodiment of the present disclosure.
Figure 3B:
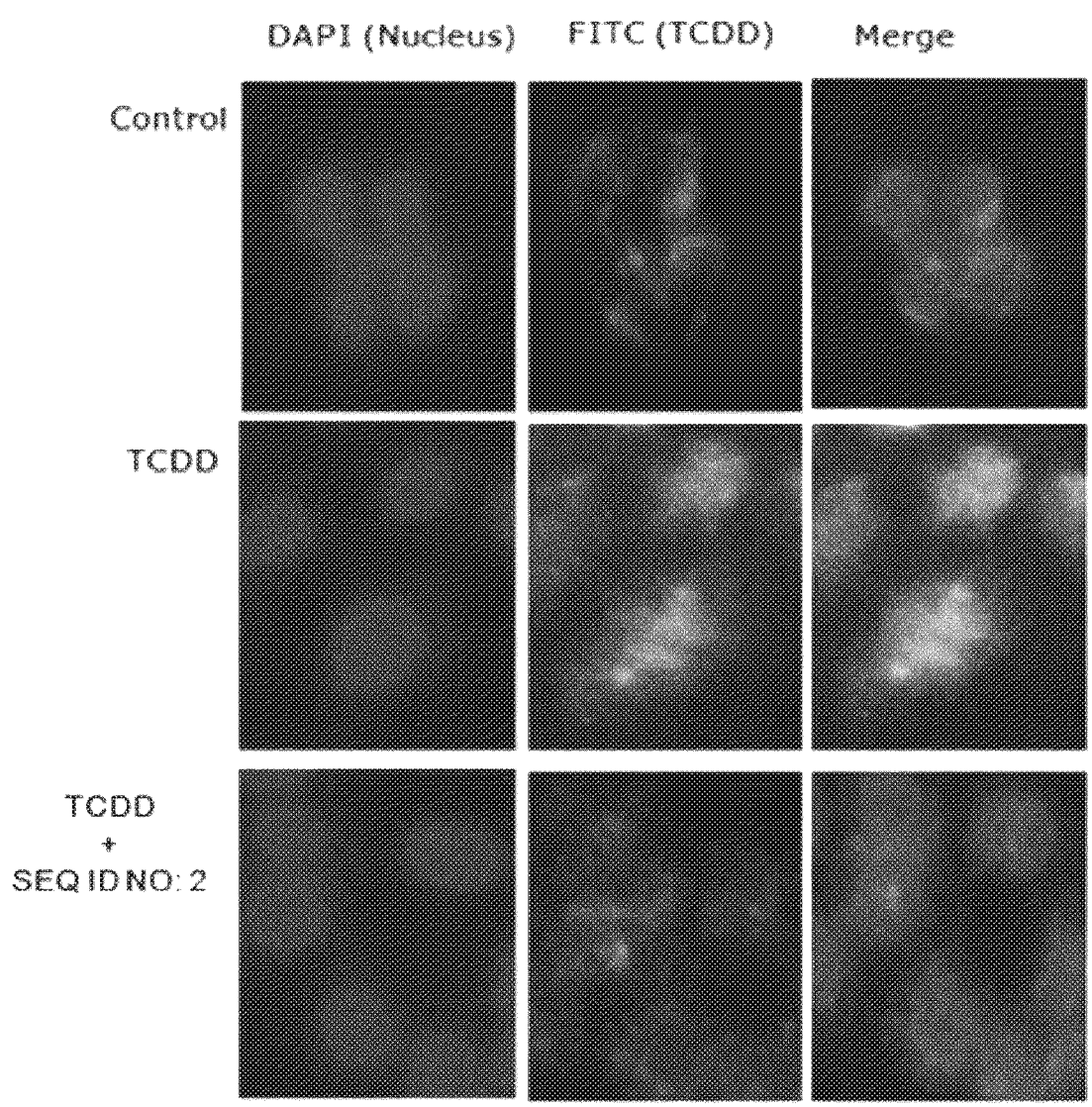
FIG. 3B is a graph showing TCDD ICC results of a peptide consisting of an amino acid sequence of SEQ ID NO: 2 according to an embodiment of the present disclosure.
Figure 3C:
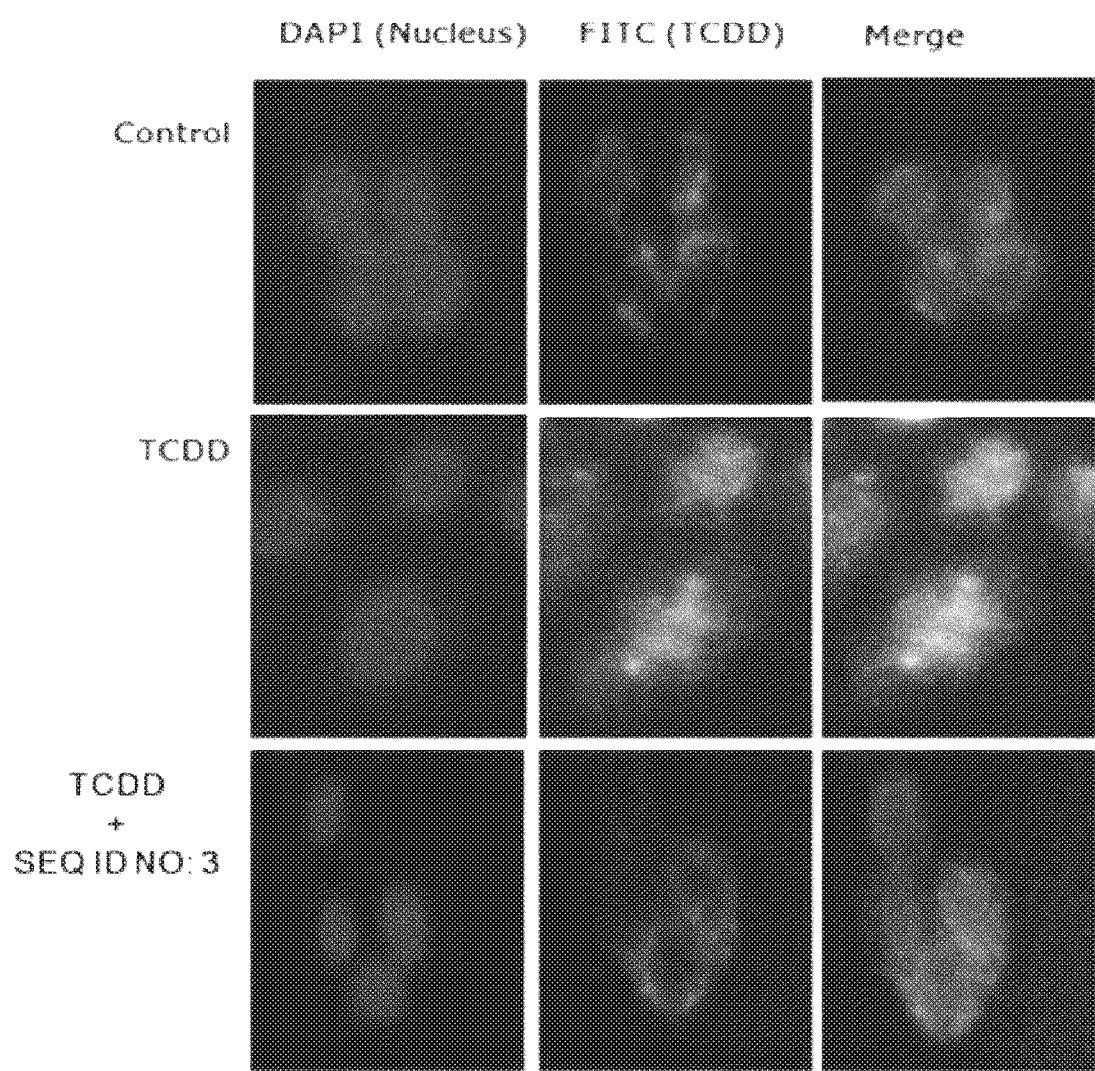
FIG. 3C is a graph showing TCDD ICC results of a peptide consisting of an amino acid sequence of SEQ ID NO: 3 according to an embodiment of the present disclosure.

As shown in FIGS. 3A to 3C, the peptide consisting of an amino acid sequence of SEQ ID NO: 1, 2, or 3 inhibited introduction of TCDD into cells.

Example 4. ROS Analysis in Cell

HaCaT cells, human keratinocyte cells, were seeded on a 6-well plate at a density of $3 \times 10^5$ cells/well and cultured overnight. Subsequently, 10 nM of TCDD and 50 µM of the peptide consisting of an amino acid sequence of SEQ ID NO: 1, 2, or 3 were added to the culture medium. After 30 minutes of reaction, the cells were treated for 24 hours and further treated with DCFH-DA for 30 minutes. Then, the cells were collected and subjected to FACS analysis to observe changes of average FL1 values, and the results are shown in FIGS. 4A to 4C.

Figure 4A:
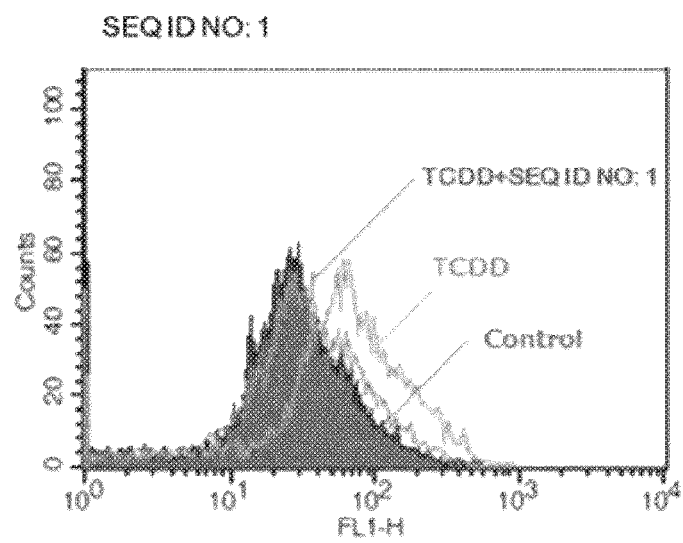
FIG. 4A is a graph showing ROS analysis results of a peptide consisting of an amino acid sequence of SEQ ID NO: 1 according to an embodiment of the present disclosure in cells.
Figure 4B:
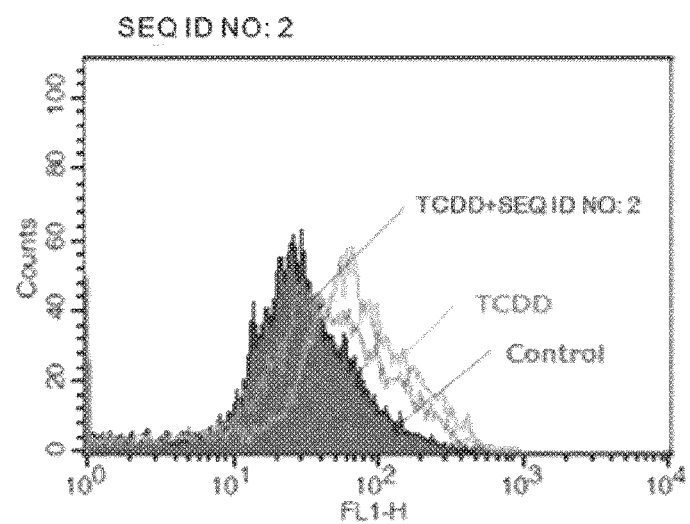
FIG. 4B is a graph showing ROS analysis results of a peptide consisting of an amino acid sequence of SEQ ID NO: 2 according to an embodiment of the present disclosure in cells.
Figure 4C:
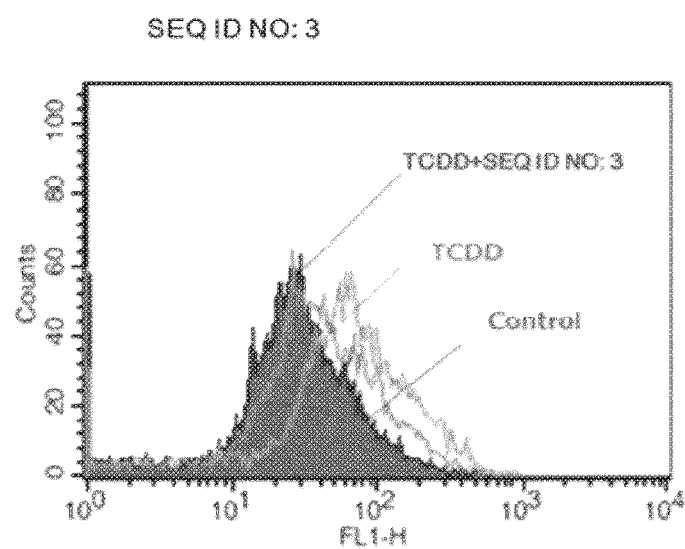
FIG. 4C is a graph showing ROS analysis results of a peptide consisting of an amino acid sequence of SEQ ID NO: 3 according to an embodiment of the present disclosure in cells.

As shown in FIGS. 4A to 4C, the peptide consisting of an amino acid sequence of SEQ ID NO: 1, 2, or 3 reduced ROS levels increased by TCDD in cells.

Example 5. RT-PCR of CYP1A1 and Inflammatory Molecules

Figure 5A:
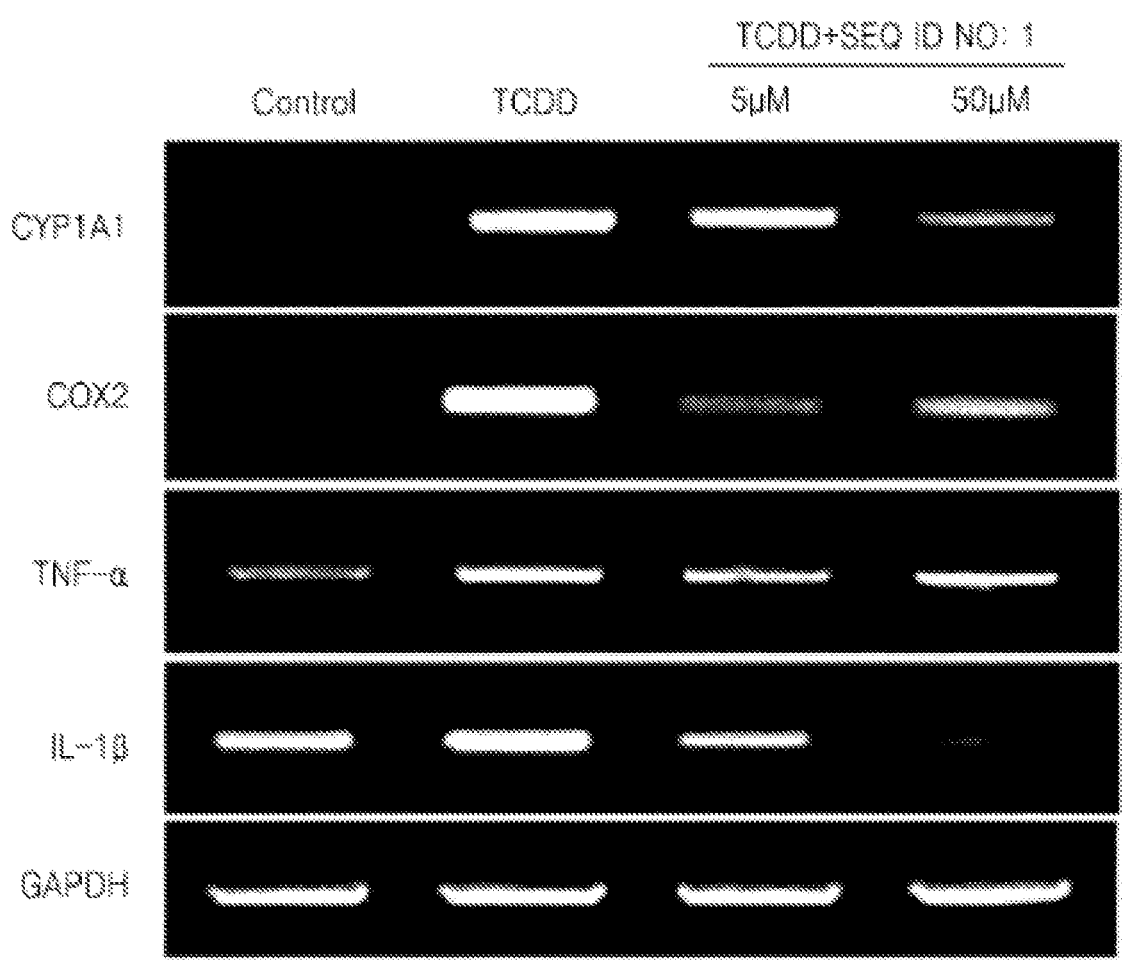
FIG. 5A is a graph showing RT-PCR results of CYP1A1 and inflammatory molecules using a peptide consisting of an amino acid sequence of SEQ ID NO: 1 according to an embodiment of the present disclosure.
Figure 5B:
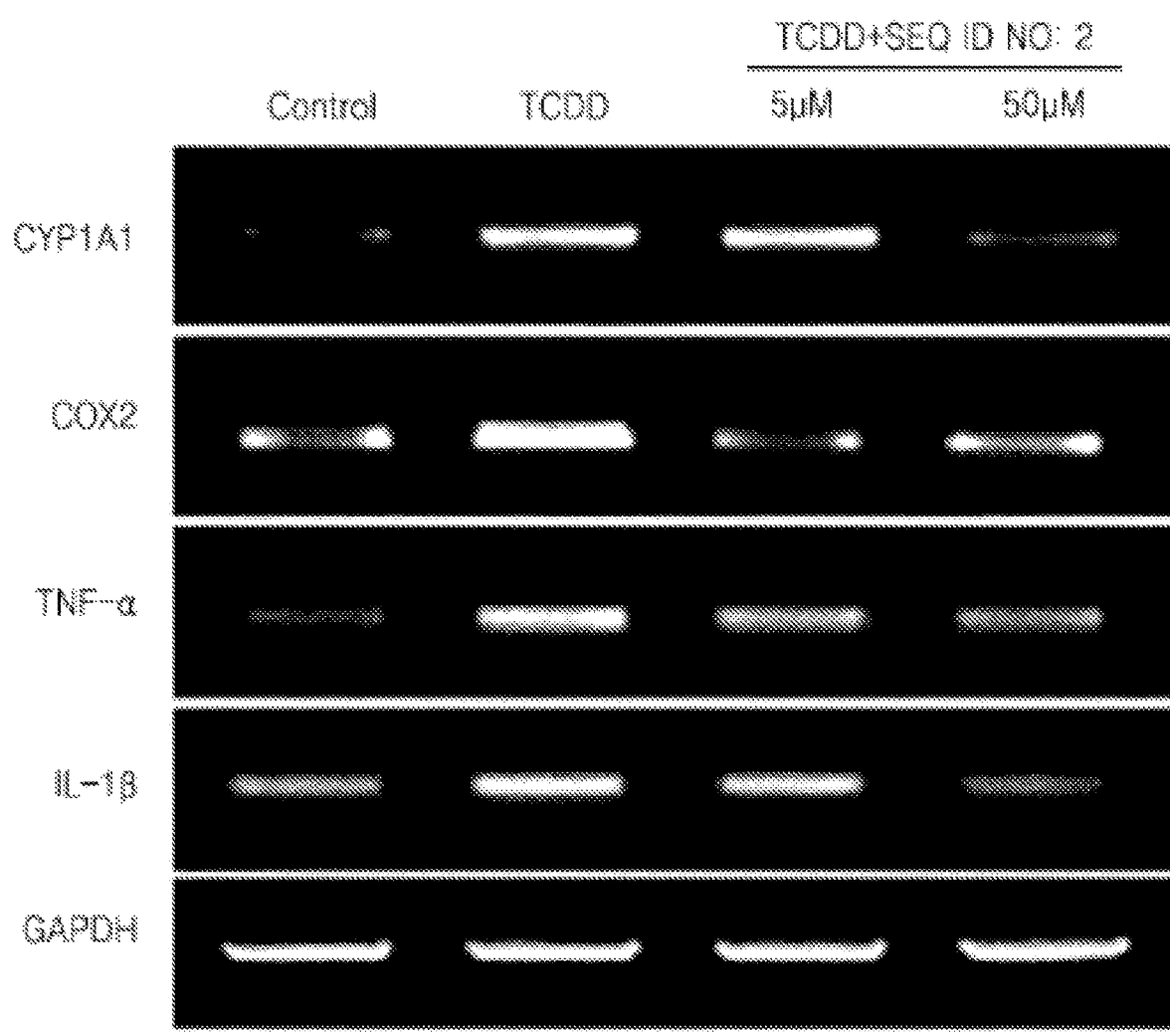
FIG. 5B is a graph showing RT-PCR results of CYP1A1 and inflammatory molecules using a peptide consisting of an amino acid sequence of SEQ ID NO: 2 according to an embodiment of the present disclosure.
Figure 5C:
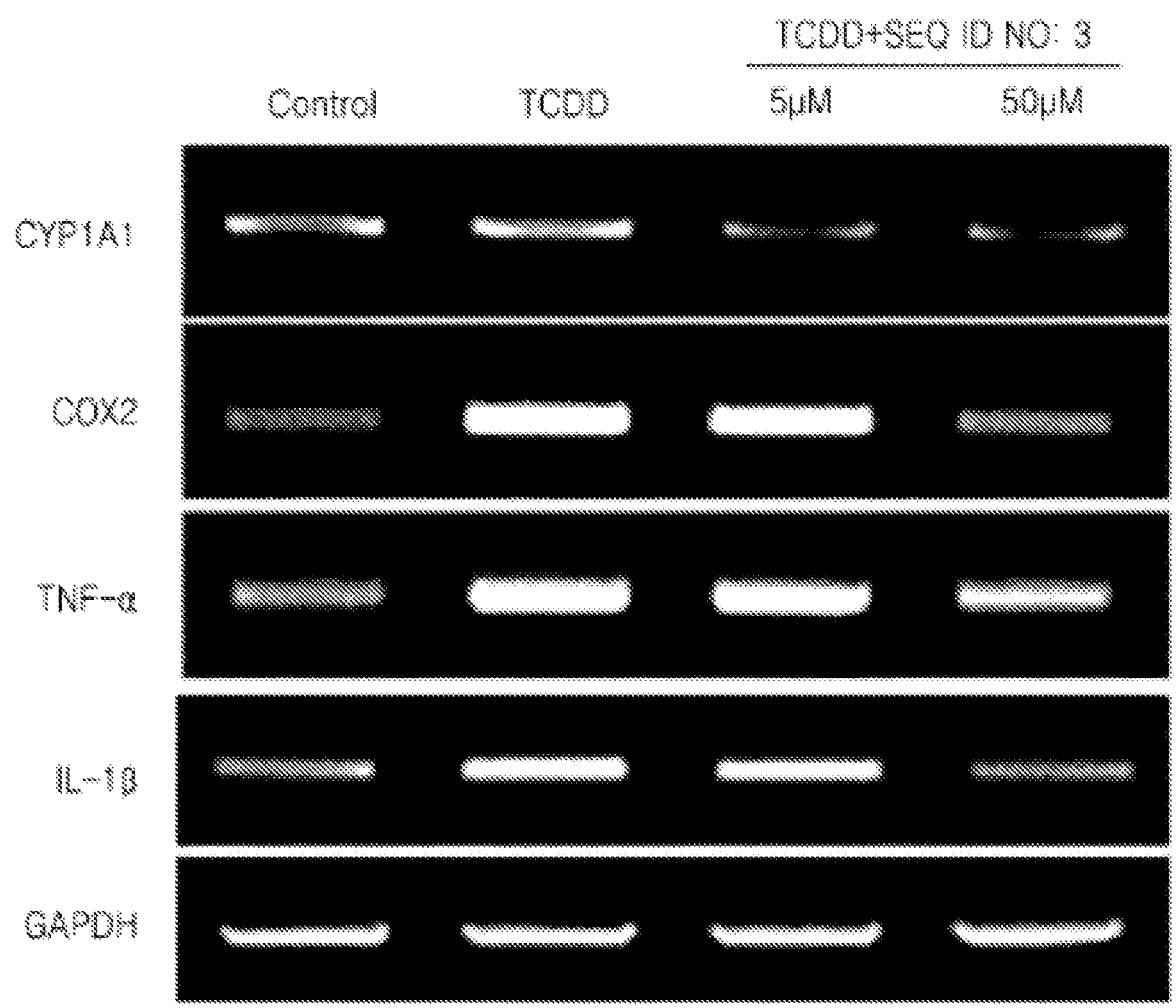
FIG. 5C is a graph showing RT-PCR results of CYP1A1 and inflammatory molecules using a peptide consisting of an amino acid sequence of SEQ ID NO: 3 according to an embodiment of the present disclosure.

HaCaT cells, human keratinocyte cells, were seeded on a 6-well plate at a density of $3 \times 10^5$ cells/well and cultured overnight. Subsequently, 10 nM of TCDD and 50 µM of the peptide consisting of an amino acid sequence of SEQ ID NO: 1, 2, or 3 were added to the culture medium. After 30 minutes of reaction, the cells were treated for 6 hours or 24 hours and collected to separate RNA therefrom. After quantifying RNA, cDNA was synthesized using a cDNA synthesis kit (Intron, Korea). Then, polymerase chain reaction (PCR) was performed using a PCR PreMix kit (Intron, Korea) and a primer for each of CYP1A1, TNF-a, IL-6, IL-1 b, and COX-2 shown in Table 4. Then, by running the resultant on a 5% agarose gel, the expression levels of mRNA of the growth factors were compared under the conditions of treating the respective samples, and the results are shown in FIGS. 5A to 5C.

TABLE 4

| SEQ ID NO: | Primer | Sequence (5'-3') |
|---|---|---|
| 4 | CYP1A1_F | GGATCTTTCTCTGTACCCTGG |
| 5 | CYP1A1_R | AGCATGTCCTTCAGCCCAGA |
| 6 | TNF-a_F | CGTCAGCCGATTRTGCTATCT |
| 7 | TNF-a_R | CGGACTCCGCAAAGTCTAAG |
| 8 | IL-6_F | AAAGAGGCACTGCCAGAAAA |
| 9 | IL-6_R | ATCTGAGGTGCCCATGCTAC |
| 10 | IL-1b_F | TTCGACACATGGGATAACGA |
| 11 | IL-1b_R | TCTTTCAACACGCAGGACAG |

TABLE 4-continued

| SEQ ID NO: | Primer | Sequence (5'-3') |
|---|---|---|
| 12 | COX-2_F | ATCATTCACCAGGCAAATTGC |
| 13 | COX-2_R | GGCTTCAGCATAAAGCGTTTG |

As shown in FIGS. 5A to 5C, the peptide consisting of an amino acid sequence of SEQ ID NO: 1, 2, or 3 had the effect of inhibiting expressions of CYP1A1 and various inflammatory factors induced by TCDD.

Example 6. AhR Nuclear Translocation Test

HaCaT cells, human keratinocyte cells, were seeded on a 6-well plate at a density of $3 \times 10^5$ cells/well and cultured overnight. 10 nM of urban particulate matter (PM, Sigma Aldrich, USA) and 50 μM of the peptide consisting of an amino acid sequence of SEQ ID NO: 1, 2, or 3 were added to the culture medium. After 30 minutes of reaction, the cells were treated for 1 hour and collected to obtain nuclei and cytoplasmic proteins separated from each other. Then, Westin blotting was performed using aryl hydrocarbon receptor (AhR) antibody (Santa Cruz Biotechnology, USA) to identify activated nuclear translocation of AhR, and the results are shown in FIGS. 6A to 6C.

Figure 6A:
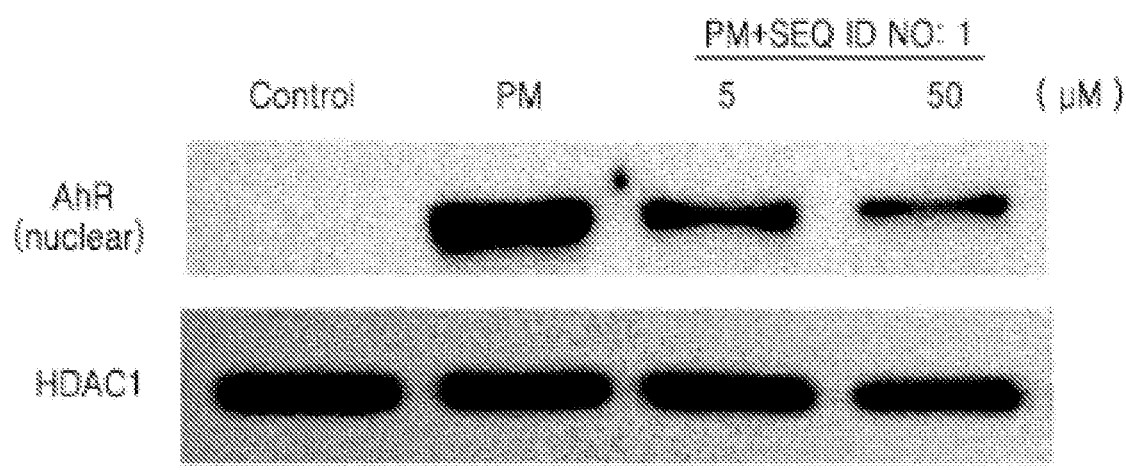
FIG. 6A is a graph showing AhR nuclear translocation test results of a peptide consisting of an amino acid sequence of SEQ ID NO: 1 according to an embodiment of the present disclosure.
Figure 6B:
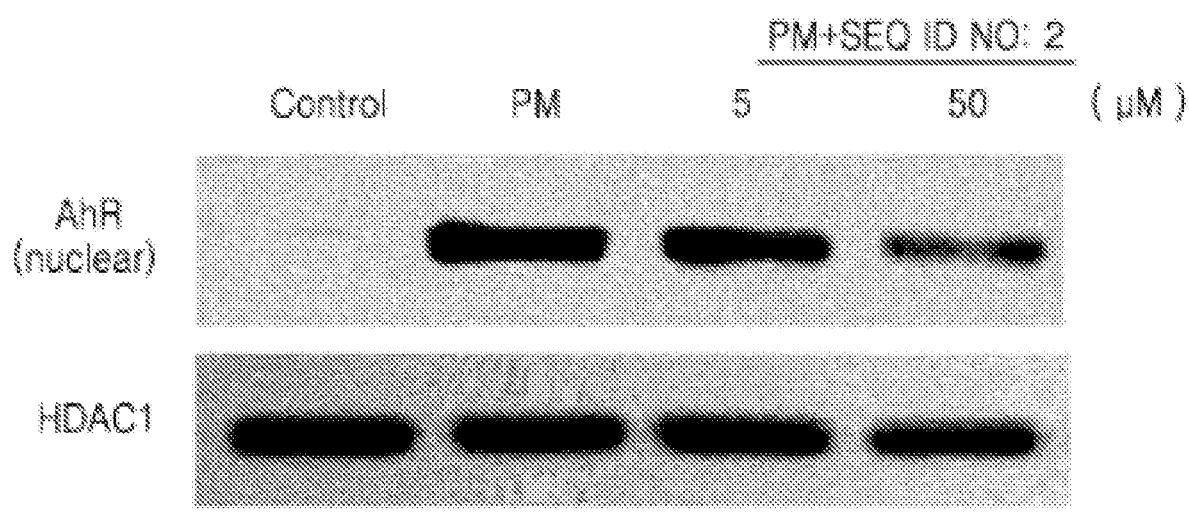
FIG. 6B is a graph showing AhR nuclear translocation test results of a peptide consisting of an amino acid sequence of SEQ ID NO: 2 according to an embodiment of the present disclosure.
Figure 6C:
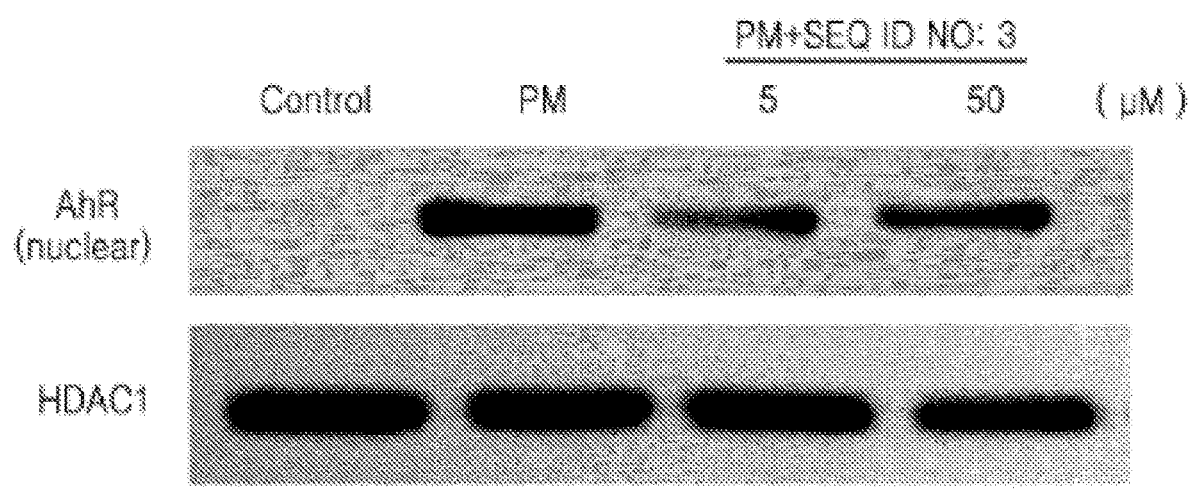
FIG. 6C is a graph showing AhR nuclear translocation test results of a peptide consisting of an amino acid sequence of SEQ ID NO: 3 according to an embodiment of the present disclosure.

As shown in FIGS. 6A to 6C, the peptide consisting of an amino acid sequence of SEQ ID NO: 1, 2, or 3 inhibited nuclear translocation of AhR by particulate matter.

Example 7. RT-PCR of CYP1A1 and Inflammatory Molecules

HaCaT cells, human keratinocyte cells, were seeded on a 6-well plate at a density of $3 \times 10^5$ cells/well and cultured overnight. Subsequently, 10 nM of particulate matter (PM) and 50 μM of the peptide consisting of an amino acid sequence of SEQ ID NO: 1, 2, or 3 were added to the culture medium. After 30 minutes of reaction, the cells were treated for 6 hours or 24 hours and collected to separate RNA therefrom. After quantifying RNA, cDNA was synthesized using a cDNA synthesis kit (Intron, Korea). Then, PCR was performed using a PCR PreMix kit (Intron, Korea) and a primer for each of CYP1A1, TNF-a, IL-6, IL-1b, and COX-2 shown in Table 5. Then, by running the resultant on a 5% agarose gel, the expression levels of mRNA of the growth factors were compared under the conditions of treating the respective samples, and the results are shown in FIGS. 7A to 7C.

TABLE 5

| SEQ ID NO: | Primer | Sequence (5'-3') |
|---|---|---|
| 4 | CYP1A1_F | GGATCTTTCTCTGTACCCTGG |
| 5 | CYP1A1_R | AGCATGTCCTTCAGCCCAGA |
| 6 | TNF-a_F | CGTCAGCCGATTRTGCTATCT |
| 7 | TNF-a_R | CGGACTCCGCAAAGTCTAAG |
| 8 | IL-6_F | AAAGAGGCACTGCCAGAAAA |
| 9 | IL-6_R | ATCTGAGGTGCCCATGCTAC |
| 10 | IL-1b_F | TTCGACACATGGGATAACGA |
| 11 | IL-1b_R | TCTTTCAACACGCAGGACAG |
| 12 | COX-2_F | ATCATTCACCAGGCAAATTGC |
| 13 | COX-2_R | GGCTTCAGCATAAAGCGTTTG |

Figure 7A:
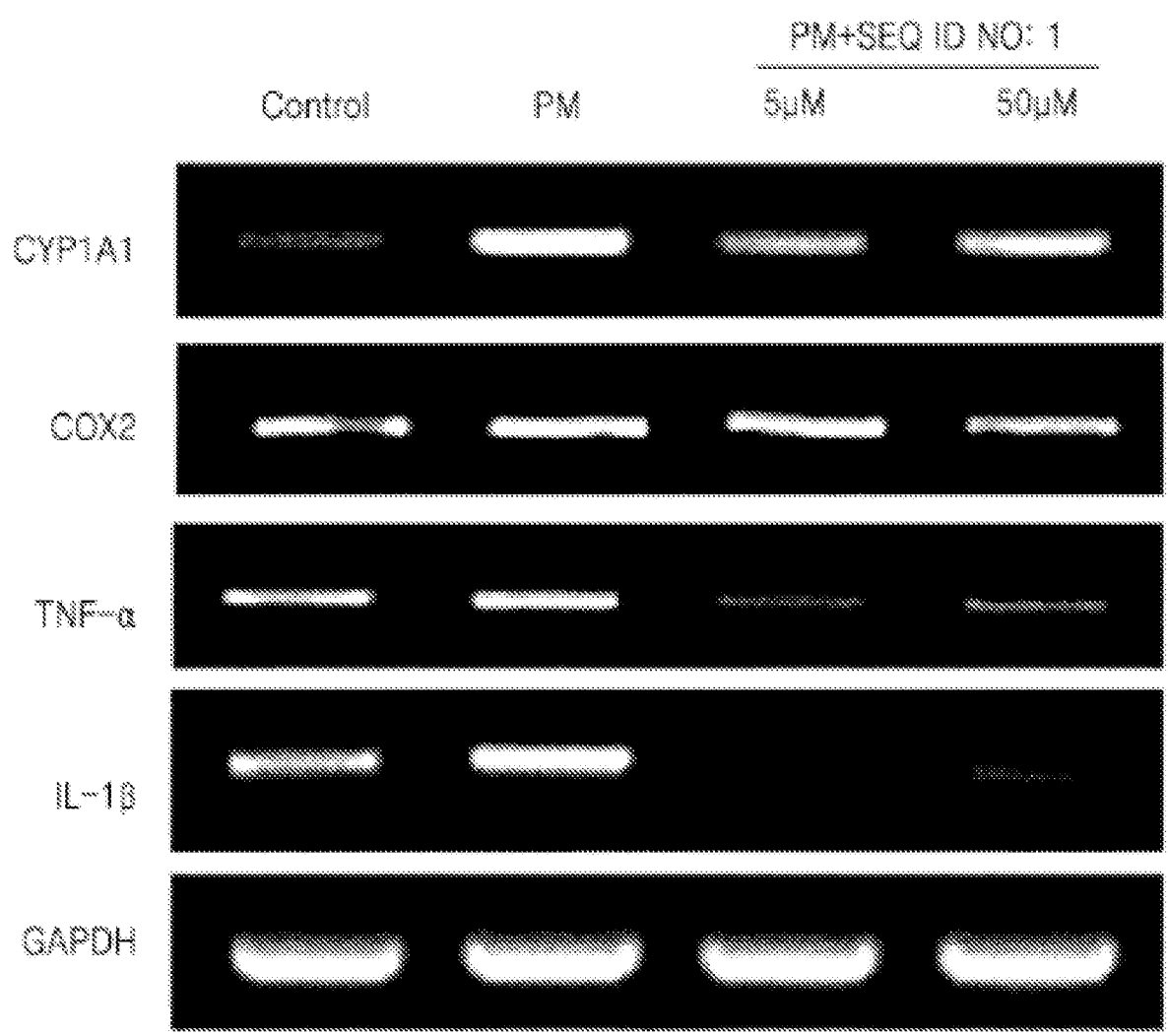
FIG. 7A is a graph showing RT-PCR results of CYP1A1 and inflammatory molecules using a peptide consisting of an amino acid sequence of SEQ ID NO: 1 according to an embodiment of the present disclosure.
Figure 7B:
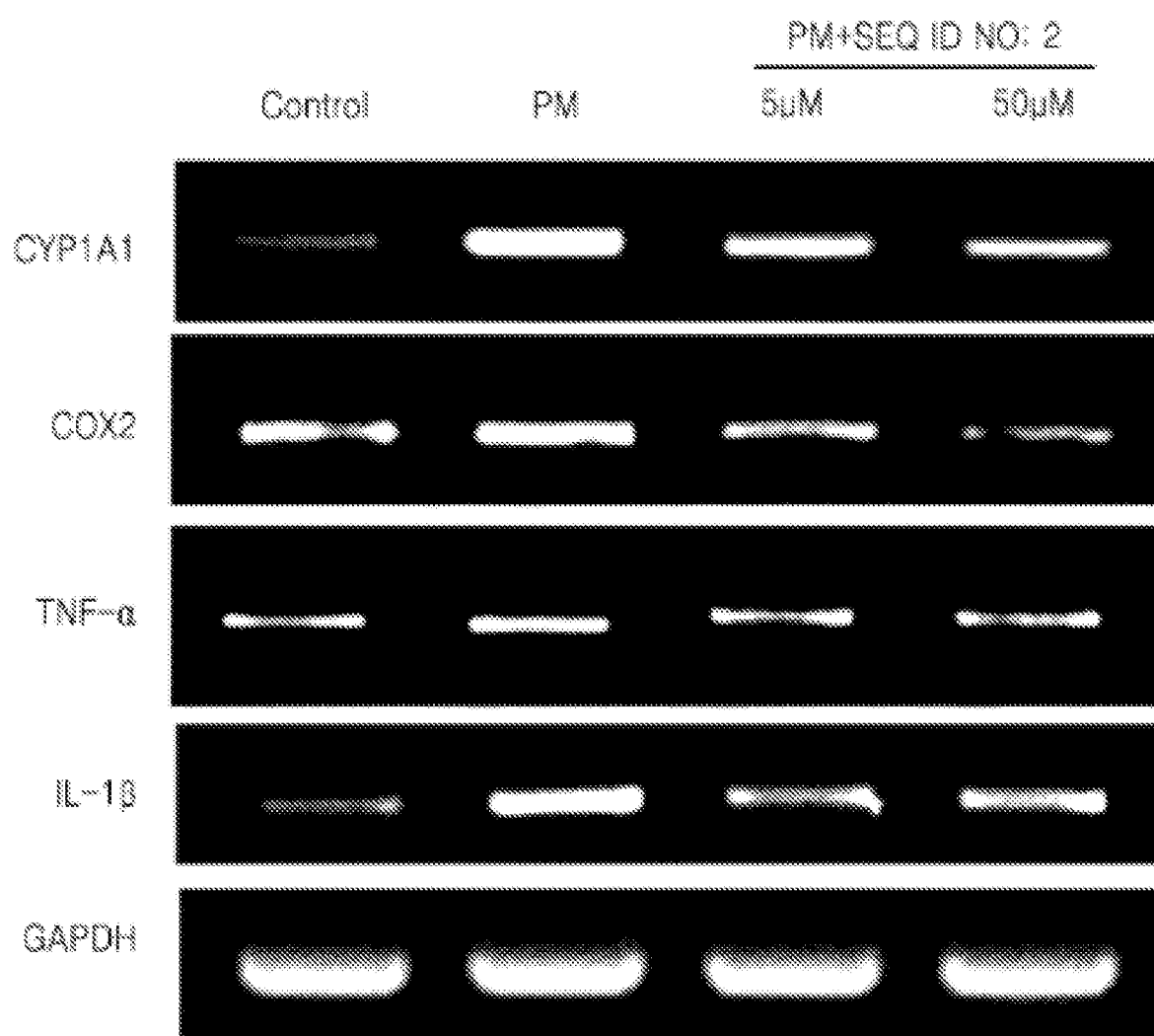
FIG. 7B is a graph showing RT-PCR results of CYP1A1 and inflammatory molecules using a peptide consisting of an amino acid sequence of SEQ ID NO: 2 according to an embodiment of the present disclosure.
Figure 7C:
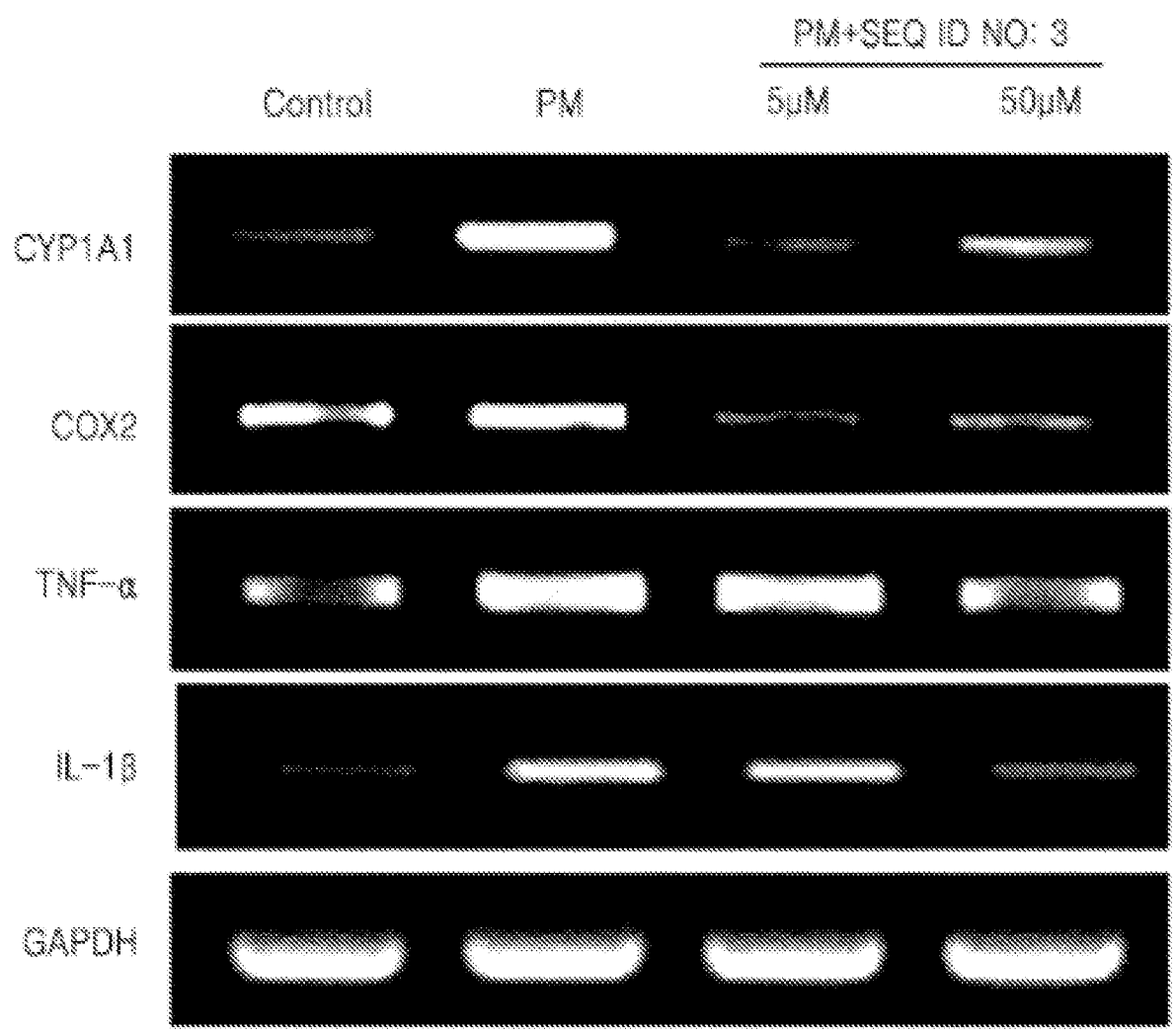
FIG. 7C is a graph showing RT-PCR results of CYP1A1 and inflammatory molecules using a peptide consisting of an amino acid sequence of SEQ ID NO: 3 according to an embodiment of the present disclosure.

As identified in FIGS. 7A to 7C, the peptide consisting of an amino acid sequence of SEQ ID NO: 1, 2, or 3 showed the effects of inhibiting expressions of CYP1A1 and various inflammatory factors induced by particulate matter.

INDUSTRIAL AVAILABILITY

The present disclosure relates to a peptide with a cytoprotective effect against environmental pollutants and a use thereof.

---

The invention claimed is:

1. A method for treating a disease caused by a dioxin or a dioxin-like substance in a subject, the method comprising administering a peptide consisting of the amino acid sequence of SEQ ID NO: 1 as an active ingredient to the subject, wherein the peptide binds to a dioxin or a dioxin-like substance, and optionally wherein the N- or C-terminus of the peptide is modified.

2. The method of claim 1, wherein the disease caused by a dioxin or a dioxin-like substance is selected from the group consisting of a skin disease, decreased sperm count, testicular cancer, prostate cancer, endometrial hyperplasia, breast cancer, hepatotoxicity, weakened immunity, hyperlipidemia, hypospadia, cryptorchidism, deformed child birth, vascular damage, hepatocellular carcinoma, hepatomegaly, adenofibrosis, weight loss, hair loss, oral edema, blepharedema, and gastric mucosal ulcer.

3. The method of claim 1, wherein the dioxin-like substance is selected from the group consisting of polychlorinated dibenzo-p-dioxin (PCDD), polychlorinated dibenzofuran (PDCF), and polychlorinated biphenyl (PCB).

4. The method of claim 3, wherein the polychlorinated dibenzo-p-dioxin is 2,3,7,8-tetrachlorodibenzo-p-dioxin (TCDD).

5. The method of claim 1, wherein the peptide comprises an N- or a C-terminal modification.

6. The method of claim 5, wherein the peptide comprises an N-terminal modification which is a protective group selected from the group consisting of an acetyl group, a fluorenylmethyloxycarbonyl group, a formyl group, a palmitoyl group, a myristyl group, a stearyl group, and a polyethylene glycol (PEG).

7. The method of claim 5, wherein the peptide comprises a C-terminal modification which is selected from the group consisting of an amino group (—NH$_2$) and an azide group (—NHNH$_2$).

\* \* \* \* \*